United States Patent
Wargo et al.

(10) Patent No.: US 7,389,689 B2
(45) Date of Patent: Jun. 24, 2008

(54) NON-POROUS ADHERENT INERT COATINGS AND METHODS OF MAKING

(75) Inventors: Christopher J. Wargo, Wellsley, MA (US); Karl Niermeyer, Tingsborough, MA (US)

(73) Assignee: Entegris, Inc., Chaska, MN (US)

( * ) Notice: Subject to any disclaimer, the term of this patent is extended or adjusted under 35 U.S.C. 154(b) by 0 days.

(21) Appl. No.: 10/590,132

(22) PCT Filed: Feb. 22, 2005

(86) PCT No.: PCT/US2005/005574

§ 371 (c)(1), (2), (4) Date: Aug. 18, 2006

(87) PCT Pub. No.: WO2005/083020

PCT Pub. Date: Sep. 9, 2005

(65) Prior Publication Data

US 2007/0190329 A1    Aug. 16, 2007

Related U.S. Application Data

(60) Provisional application No. 60/546,680, filed on Feb. 20, 2004, provisional application No. 60/636,565, filed on Dec. 16, 2004.

(51) Int. Cl.
*G01F 15/14*    (2006.01)

(52) U.S. Cl. .................................................. 73/432.1
(58) Field of Classification Search ............... 73/432.1; 204/450, 454
See application file for complete search history.

(56) References Cited

U.S. PATENT DOCUMENTS

2002/0043463 A1    4/2002    Shenderov
2002/0044523 A1    4/2002    Oshima et al.

OTHER PUBLICATIONS

Saeki, Fusayo, et al, Polym. Mat. Sci. Eng. (2001), vol. 85, pp. 12.
Moon, Hyejin, et al, J. Appl. Phys., (2002), vol. 92, pp. 4080.

*Primary Examiner*—Andre J Allen
(74) *Attorney, Agent, or Firm*—John E. Pillion; Timothy J. King

(57) ABSTRACT

The present invention include non-porous adherent coatings of chemically inert high purity poly-oligomers deposited on substrates. The coatings are applied and cured on the substrates at relatively low temperatures which permits the coating process to be performed with temperature sensitive structures such as magnets, electronic circuits, electrodes, and bonding pads in place on the substrate. Coated substrates, such as sensors and fluid conduits, have an effective thickness of the protective non-porous coating that is chemically bonded to a surface of the substrate that will be contacted with a fluid. The adherent non-porous coating on the substrate protect it from corrosion, particle generation, swelling, or delamination caused by contact with the fluid.

21 Claims, 7 Drawing Sheets

NON-POROUS ADHERENT INERT COATINGS AND METHODS OF MAKING

CROSS REFERENCE TO RELATED APPLICATIONS

This application clams the benefit of U.S. Provisional Application No. 60/546,680 filed Feb. 20, 2004 and U.S. Provisional Application No. 60/636,565 filed Dec. 16, 2004 the contents of these applications incorporated by reference in their entirety into the present disclosure.

BACKGROUND

There is a continuous effort to develop pressure sensors, chemical sensors, and housing materials that are lower in cost and smaller in size, yet are characterized by high reliability, sensitivity, and linearity. For example, multiple pressure sensors, temperature, and optical sensors having sensing diaphragms, cavities, and resistive elements can be made on a single silicon wafer using semiconductor fabrication processes. In the processing of such cells, sensor elements such as the thin diaphragm of a pressure sensor are formed in a silicon wafer through preferential chemical etching. Ion implantation and diffusion techniques are then used to drive doping elements into the diaphragm, forming resistive bridge circuit elements whose electrical resistance changes with strain. As a result, deflection of the diaphragm causes a change in resistance value of the piezoresistive elements, which can then be correlated to the magnitude of the pressure applied to the diaphragm.

The use of standard single-crystal silicon wafers and standard semiconductor device fabrication processes allows many such cells to be fabricated from a single wafer, providing some economy of scale. However, silicon is susceptible to chemical attack, particle generation, and erosion by various media, particularly in applications where a high-pressure, temperature, and corrosive fluids are to be sensed, e.g., semiconductor manufacturing, long term medical implants, and automotive applications. One particularly difficult and sensitive application of integrated circuits, semiconductors and metal electrodes is in electrical or electronic device implantation in a human or animal body. Extra-cellular fluids within the body are saline, and often contain a number of other ions or other electrolytes. At body temperatures, severe and rapid corrosion may lead to rapid and untimely failure of the device. For such applications, a pressure, temperature, or chemical sensor and fluid handling devices in contact with these fluids (i.e. catheters, pumps, heat exchangers, or conduits) must also be of high chemical purity, physically rugged and resistant to the hostile environment of the sensed medium. It would be advantageous that a micromachined silicon sensor cell include some form of protection in order to realize its superior operational characteristics in the chemically hostile environment. Current methods for producing media-compatible, high-pressure sensors include enclosing a silicon sensing chip in an inert fluid, such as a silicone oil or gel, and then further separating the sensing chip from the medium to be sensed with a metal diaphragm, such that pressure must be transmitted through the metal diaphragm and fluid to the sensing chip. While achieving some of the operational advantages of silicon pressure transducer cells, the manufacturing processes for these sensors are relatively expensive and complicated.

Piezoelectric and capacitive pressure sensors are typically thin ceramic plates or diaphragms that may be coated with thick-film electrodes or bridge elements to form capacitors or strain sensing elements. However, each of these also have certain disadvantages, such as complex circuitry to detect capacitance changes, the requirement for ceramic-to-ceramic bonds, and a maximum pressure capability typically not exceeding about 1000 psi (about 7 MPa). For higher pressures, metal diaphragms have found use as the sensing element, however these diaphragms are not generally useful in corrosive aqueous solutions. Metal diaphragms generally deflect more for a given thickness and pressure than ceramic diaphragms. With metal diaphragms bridge elements or electrodes may be deposited on to a dielectric insulating layer on the metal followed by thin-film polysilicon or metal deposited on the metal diaphragm to form the bridge or electrode structures. For example, a thin-film polysilicon layer is deposited on the dielectric to form the piezoresistors of the bridge, followed by thin-film metallization to provide electrical interconnects. As is conventional, the thin-film layers are typically deposited by such processes as chemical or physical vapor deposition. The equipment necessary for these processes is expensive, and deposition rates are extremely slow and difficult to use with complex structures and large structures like housings, bellows, or conduits. Deposition of the thin-film layers requires multiple patterning, exposure, developing and stripping steps for the required thin-film photoresists and metallization, and must be carried out in a controlled environment to assure that no air borne particles are present on the surface to be coated. In addition, because such processes deposit thin-films usually no thicker than 10,000 angstroms, the surface of the metal diaphragm must be extremely smooth to avoid rough surface features penetrating through or producing discontinuities in the deposited thin films. Finally, the resistance of the resulting polysilicon thin-film piezoresistors can vary dramatically with temperature.

Typically, a sensor is contained within a chemically and mechanically protective housing. The housing essentially surrounds the sensor and any associated electronics for sensor excitation and signal processing. While this provides mechanical protection for the sensor, protection from hazardous chemicals and contaminants in the medium must also be provided. In one type of pressure sensor assembly, a silicone gel, fluorosilicone gel, or silicone oil is applied over the external surface of a pressure sensor and essentially partially fills the housing in which the pressure sensor is mounted. The gel or oil is covered with a membrane. The manufacture of these cells can be cumbersome and expensive.

Various materials have been developed to provide an electrically insulative moisture barrier over a substrate. Among the more prominent of these are aromatic polyimides such as those sold under the trade designation "Kevlar" by E.I. DuPont de Nemours, & Co. However, polyimides are highly viscous, difficult to deposit, and can easily entrain gas bubbles leading to film defects. Parylene N coatings are produced by vaporizing a di(p-xylylene) dimer, pyrolyzing the vapor to produce p-xylylene free radicals, and condensing a poly-oligomer from the vapor onto a substrate that is maintained at a relatively low temperature, typically ambient or below ambient. Parylene N is derived from di(p-xylylene), while parylene C is derived from di(monochloro-p-xylylene), and parylene D is derived from di(dichloro-p-xylylene).

Although parylenes have generally advantageous electrical, chemical resistance and moisture barrier properties, it has been found that these poly-oligomers do not adhere well to many substrate surfaces, particularly under wet conditions. Although these poly-oligomers are quite resistant to liquid water under most conditions, they are subject to penetration by water vapor which may condense at the interface between the parylene film and the substrate, forming liquid water which tends to delaminate the film from the substrate. Vapor deposited parylene films are also generally quite crystalline and are subject to cracking which may also create paths for penetration of moisture to the substrate surface. Parylene has been used to protect devices and larger substrates, or a thermally bonded fluorinated polymer casing has been used. Both have been found to offer relatively poor performance in critical applications. The parylene coatings suffer from high diffusion rates, and the thermally bonded devices, provided the devices or substrate can tolerate the processing conditions, have been known to undergo mechanical stress cracking at the bond seams.

These organic coatings may be used either alone or together with fluorosilicone gels. Fluorosilicone gels are used to protect the sensor device, wirebonds, portions of the package, and leads. Fluorosilicone gels have several disadvantages including an incompatibility with fuels (e.g., swelling).

SUMMARY

This invention relates to protective coatings on sensor substrates, optical substrates, housings, or fluid handling substrates that provide a tough, adherent, insulating coating that constitutes a barrier against penetration of fluids and ions to the surface of the sensor, electrodes, other structure deposited on the substrate. The protective coating may also be applied to housing surfaces, or other structures in contact with fluids like impellers, flexible bellows members, and mixers.

Embodiments of the present invention include structures or substrates having an effective thickness of a protective non-porous coating that is adherent and chemically bonded to a surface of the structure in contact with a fluid. Structures coated may be but are not limited to a sensor, a conduit, a vessel such as a cuvette or gas sampling cell, bellows, surfaces of fluid handling equipment, or transparent windows that are to be contacted with a fluid during chemical processing and preferably a fluid whose properties are to be measured, characterized, or transported. The protective and adherent coating is chemically inert and has low permeability to fluids, ions and gases. The adherent non-porous coating on a surface of the structure reduce or protect it and structures formed on the structure such as electrodes and electrical structures from corrosion, particle generation, delamination, and swelling. The coating on the surface of the structure can reduce or prevent changes in response, sensitivity, or performance caused by the adverse effects of the fluid in contact with the underlying substrate. The coating is prepared from a coating material that includes a solvent and a poly-oligomer or poly-oligomer that contains fluorine and reactive groups for chemically bonding a portion of the poly-oligomer to the sensor surface. The adherent coating can be formed by evaporation of solvent from a bubble free volume of coating material deposited onto the sensor surface to form a non-porous film. The non-porous film may be cured to form the protective non-porous coating; the coating adheres to the substrate surface and at least a portion is chemically bonded to the surface of the sensor. The curing preferably occurs at a temperature that does not adversely affect the underlying substrate and can be less than the boiling point of the coating material solvent(s) and less than the Tg of poly-oligomer film. The curing may include the act of ramping the temperature up to a value greater than the boiling point of the solvent and greater than the Tg of the poly-oligomer material to remove any remaining solvent and to enhance the adhesion of the coating to the ceramic substrate. The cured film have a density, thickness, and mass which permits the substrate or sensor to function in a device or produce a measurable physical response to energy input. The coating protects or reduces the effects of corrosive fluids to the underlying substrate or to the sensing device and protects them from particle generation, degradation, swelling, or corrosion especially in high purity corrosive fluids.

Embodiments of the present invention include fluid contacting structures having an effective thickness of a protective non-porous coating that is adherent and chemically bonded to a surface of the structure in contact with a fluid. The non-porous coating protects the underlying structures from corrosion, swelling, particle generation, delamination, or generation of contamination. Structures coated with the non-porous adherent coating in contact with a fluid may include but are not limited to sensors, conduits, a vessel such as a cuvette, pump housings, mixers, stirrers, impellers, gas sampling cell, bellows, material handling equipment like pumps, flow meters, or flow controllers or transparent windows that are to be contacted with a fluid during chemical processing. The housing may be made of a chemically suitable material, preferably a material which is chemically inert to the fluid. Some housing materials may include a coating of the poly-oligomeric material applied to a portion or all of the housing surfaces. The protective and adherent coating is chemically inert, has low permeability to fluids, ions and gases. The adherent non-porous coating on various substrate surfaces protect the substrate from corrosion, particle generation, delamination, or chemical and or physical changes caused by the fluid. The coating is prepared from a coating material that includes a solvent and a poly-oligomer or poly-oligomer that contains fluorine and reactive groups for chemically bonding a portion of the poly-oligomer to the substrate surface. The adherent coating can be formed by evaporation of solvent from a bubble free volume of coating material deposited onto the substrate surface to form a non-porous film. The non-porous film can be cured to form the protective non-porous coating; the coating adheres to the substrate surface and at least a portion is chemically bonded to the surface of the substrate. The curing preferably occurs at a temperature less than the boiling point of the coating material solvent(s) and less than the Tg of poly-oligomer film. The curing may include the act of ramping the temperature up to a value greater than the boiling point of the solvent and greater than the Tg of the poly-oligomer material to remove any remaining solvent and to enhance the adhesion of the coating to the substrate. The cured film can have a density, thickness and mass which permits the substrate to operate or function in a material or fluid handling device. The non-porous adherent coating protects that portion of the material handling article from particle generation, degradation, and corrosion especially in high purity corrosive fluids, and materials such as slurries.

One embodiment of the present invention is a sensor having a surface with an effective thickness of an adherent protective coating on the surface of the sensor for contacting a fluid to be measured. The property of the fluid to be measured may include but is not limited to pressure, flow, temperature, chemical composition, chemical purity, or a combination of these. The coating is preferably an adherent non-porous coating on a surface of the sensor which protects it and structures formed on it from corrosion, particle generation, delamination, or changes in sensor response and sensitivity caused by the fluid. The coating includes a soluble poly-oligomer containing fluorine, that is chemically bonded to the sensor surface to form an adherent protective coating. The adherent coating can be formed by curing a non-porous evaporated film of the coating material formed or placed on the surface of the sensor. Preferably the curing occurs at a temperature less than the boiling point of the coating material solvent and less than the Tg of poly-oligomer film. The curing may include the act of ramping the temperature up to a value greater than the boiling point of the solvent and greater than the Tg of the poly-oligomer material to remove any remaining solvent and to enhance the adhesion of the coating to the ceramic substrate. The device and sensor may include structures for probing by electrical energy, light energy, mechanical energy, or chemical interaction the state of the sensor and means or structures for measuring said physical response of said sensor to the excitation. Such structure on one or more of the sensor surfaces may include but are not limited to resistive, capacitive, transistors, electrical contacts, optical contacts, or a combination of these. The sensor includes a ceramic material. Preferably the non-porous film of the coating material formed or placed on the surface of the sensor includes greater than 10% of the poly-oligomer in the coating material deposited on the substrate to form the non-porous film. The sensor may be used to measure one or more fluid properties such as but not limited to temperature, flow, chemical purity, pressure, or a combination of these. The poly-oligomer coating material deposited or applied to the sensor surface can include an organosilane adhesion promoter. The adherent protective coating can be formed on one or more surfaces of the sensor. Preferably the adherent protective coating is more than 50 microns thick. The sensor surface can be treated to chemically bond the poly-oligomer to the sensor surface. The poly-oligomer may bond to surface groups that includes but are not limited to reactive amine, hydroxyl, carboxylic, ester, amide, or thiol groups for bonding the fluorine comprising poly-oligomer to the sensor surface.

Another embodiment of the present invention is a method for measuring a fluid property such as pressure, flow, temperature, chemical composition, chemical purity, or a combination of these in for example a fluid sample or fluid in a conduit. The method includes contacting fluid with a sensor having a surface with an effective thickness of an adherent protective coating on the surface of the sensor for contacting the fluid to be measured. The adherent coating includes a soluble poly-oligomer containing fluorine where a portion of the poly-oligomer is chemically bonded to the sensor surface to form an adherent protective coating. The adherent coating is formed by curing a non-porous film of the coating material formed or placed on the surface of the sensor. Preferably curing occurs at a temperature less than the boiling point of the coating material solvent and less than the glass transition temperature, Tg, of poly-oligomer film. The curing may include the act of ramping the temperature up to a value greater than the boiling point of the solvent and greater than the Tg of the poly-oligomer material to remove any remaining solvent and to enhance the adhesion of the coating to the ceramic substrate. Applying energy to the adherent coated sensing device, measuring the physical response of the sensor, and comparing the physical response to a standard relationship allows correlation of the coated sensor's physical response to a property of the fluid such as but not limited to pressure, temperature, purity, flow or a combination of these. The method can be performed using a coated sensor that is a piezoresistive, piezoelectric, or thermoresistive material. The method may be performed using a coated sensor that includes one or more plates in capacitive sensor, the sensor having two plates and an adherent non-porous perfluorinated coating positioned on one of the plates surfaces in contact the fluid.

Another embodiment of the present invention is a method of making a coated sensor that includes forming a non-porous film of a coating material deposited on a chemically bondable fluid contacting surface of a sensor. The non-porous film of coating material includes a soluble poly-oligomer containing fluorine and reactive groups on the poly-oligomer. At least a portion of the poly-oligomer reactive groups are chemically reacted with groups on the surface of the sensor for bonding at least a portion of the poly-oligomer to the chemically bondable fluid contacting surface of the sensor. The non-porous film on the chemically bondable fluid contacting surface of the sensor includes greater than 10% of the poly-oligomer deposited to form the non-porous film, and preferably little or no coating material is wasted. The non-porous film may be formed by evaporation of the solvent from the coating material deposited on the sensor, alternatively a film of non-porous material may be placed on the sensor surface. The non-porous film of the coating material is cured on the chemically bondable fluid contacting surface of a sensor with the curing chemically bonding the poly-oligomer reactive groups to the chemically bondable surface of the sensor surface to form an adherent protective coating on the surface of the sensor. The non-porous film of the coating material on the chemically bondable fluid contacting surface of the sensor is formed by removing solvent from a solution of the poly-oligomer contacting surface of the sensor. The curing step preferably occurs at a temperature below which damage to resistive structures like, capacitors, transistors, electrical contacts, optical contacts, or a combination of these may result. Preferably curing occurs at a temperature less than the boiling point of the coating material solvent and less than the Tg of poly-oligomer film and includes another act of ramping the temperature up to a value greater than the boiling point of the solvent and greater than the glass transition temperature, Tg, of the poly-oligomer material to remove any remaining solvent and to enhance the adhesion of the coating to the ceramic substrate. Even more preferably the curing is at a temperature of less than about 120° C. The method may be performed where the fluorine containing poly-oligomer includes an aliphatic ether ring in the chain of the poly-oligomer. In the method, the fluid contacting surface can be cleaned and made chemically bondable by a treatment chosen such as but not limited to plasma etching, chemical modification with an adhesion promoter, oxidation, or hydroxylation of a surface. The sensor used in the method may include on one or more of its surfaces structures such as but not limited to resistor bridges, resistors, capacitors, electrodes, transistors, electrical contacts, optical contacts, bonding pads or a combination of these. The coating material may include an organosilane adhesion promoter to react with the sensor surface and also the reactive groups in the poly-oligomer to bond at least a portion of the poly-oligomers to the sensor surface to form an adherent protective film on the sensor surface. The method may be used to form an adherent protective coating on the surface of the sensor that can have a thickness of greater than 50 microns, a thickness greater than 100 microns, a thickness of greater than 2,500 microns. Multiple coatings may be deposited on the substrate and cured. The method of coating may be used to coat a sensor diaphragm. The method may have the sensing means or structures such as but not limited to electrodes, resistive bridge structures, thermistors, optical and electrical input and output connections, formed on a surface of the sensor prior to coating and prior to curing with the coating material. The method may involve solvent removal from coating material applied to the sensor surface to form the non-porous film where the evaporation is performed in an antistatic environment. The method may use curing that can be but is not limited to chemical curing, thermal curing, photochemical curing or a combination of these.

Another embodiment of the present invention is a sensing device for measuring the property of a fluid such as but not limited to pressure, flow, chemical purity, chemical composition, or a combination of these. The device includes a sensor having a surface with an effective thickness of an adherent protective coating on a surface of the sensor that is used for contacting a fluid to be measured. The coating includes a soluble poly-oligomer containing fluorine, where at least a portion of the poly-oligomer is chemically bonded to the sensor surface to form an adherent protective coating. The adherent coating can be formed by curing a non-porous evaporated film of the coating material formed or applied on the fluid contacting surface of the sensor. The device includes structures or means for applying energy to sensing device for excitation and means or structures for measuring the physical response of the sensor to the excitation and the fluid. The device includes a housing which isolates the fluid contacting and coated side of the sensor from the interior of the housing. The housing prevents fluid communication between the non-porous adherent film of the coating material formed on the fluid contacting surface of the sensor from a second fluid isolated surface of the sensor which may have circuit elements, bonding pads, and other structures deposited onto it. The device can have a sensor with a formed adherent protective coating that has a surface energy of less than 30 dynes/cm. The housing used to mount one or more sensors may include fluid inlet and fluid outlet connections. The device may include sensor materials which include but are not limited to piezoresistive, piezoelectric, thermoresistive or a combination of these properties. Preferably the device has a sensor where the non-porous (evaporated) film of the coating material formed on the surface of the sensor includes greater than 10% of the poly-oligomer in the coating material deposited on the sensors to form the film; little or no coating material is lost during the deposition and non-porous film forming process. More preferably, greater than 70%, and even more preferably about 100% of the poly-oligomer in the coating material that was deposited on the sensor to form the coating film remains on the sensor surface; no reclamation or recycling of valuable perfluorinated coating materials or coupling agents etc. is needed, nor are excessive amounts of volatile perfluorinated solvents associated with waste streams discharged. The device and mounted sensor may be used to measure one or more fluid properties such as but not limited to temperature, flow, purity, chemical composition, pressure, or a combination of these. The device in a preferred embodiment has a sensor that is coated with a poly-oligomer that includes a fluorine containing aliphatic ether ring structure in the poly-oligomer chain.

Another embodiment of the present invention is a sensing device for measuring the flow of a fluid comprising: one or more sensors, each sensor having a surface with an effective thickness of an adherent protective coating on a surface of the sensors for contacting a fluid to be measured. The coating includes a soluble poly-oligomer containing fluorine, the poly-oligomer chemically bonded to the sensor surface forms an adherent protective coating. The adherent coating is formed by curing a non-porous film of the coating material deposited on the fluid contacting surface of the sensors. The device can include a conduit for directing fluid so that it contacts the coated sensor surface. Structures or means for applying energy, such as exciting the sensing device and means or structures for measuring the physical response from the sensors may be present on a surface of the sensors. The device includes a housing that is configured to prevent fluid communication between the non-porous adherent film of the coating material formed on the fluid contacting surface of the sensors and a second fluid isolated surface of the sensors. Each sensor of the device is fluidly sealed to the housing and separated one from the other by a fluid conduit. Preferably the sensors in the device have a film of the coating material formed on the surface of the sensors that includes greater than 10% of the poly-oligomer in the coating material deposited on the sensors to form the film. The sensors in the device may have an adherent protective coating on their surface which has a surface energy of less than 30 dynes/cm. The device can have sensors that include but are not limited to a material chosen from the group consisting of a piezoresistive, piezoelectric, ceramic, a metal, or a combination of these. The fluid conduit separating said sensors in the device may be a tube and the sensors are pressure sensors. The fluid conduit separating said sensors in the device may be a venturi and the sensors are pressure sensors. The fluid conduit separating the sensors in the device can be an orifice and the sensors can be pressure sensors. The fluid conduit separating the sensors in the device can be a tube and the sensors can be pressure sensors. The fluid conduit may be a laminar flow element from a thermal mass flow meter, where the conduit is coated on its fluid contacting inner diameter with the coating material to form the effective thickness of an adherent protective coating on the surface of the sensors for contacting a fluid to be measured; the resistive heating and temperature sensing elements of the thermal flow sensor are wound or deposited on the outside of the tube.

Another embodiment of the present invention is a sensing device that includes a sensor having a surface with an effective thickness of an adherent protective coating. The coating including a soluble poly-oligomer with a fluorine containing aliphatic ether ring structure in the poly-oligomer chain. The poly-oligomer chemically bonds to a sensor surface to form an adherent coating. The adherent coating may be formed by curing a non-porous evaporated film of the coating material formed on or deposited on the surface of the sensor to be coated. Preferably curing occurs at a temperature less than the boiling point of the coating material solvent and less than the Tg of poly-oligomer film. The curing may include the act of ramping the temperature up to a value greater than the boiling point of the solvent and greater than the Tg of the poly-oligomer material to remove any remaining solvent and to enhance the adhesion of the coating to the sensor surface, preferably the sensor surface is a ceramic substrate. The non-porous film of the coating material formed on the surface of the sensor in the device preferably includes greater than 10% of the poly-oligomer in the coating material deposited on the substrate to form the non-porous film. The sensing device preferably has a coating on the sensor of effective thickness to protect the underlying sensor from corrosion, erosion, delamination, or particle generation and the adherent protective coating permits the sensor to produce a measurable physical response to a fluid property.

Another embodiment of the present invention is a method of making a coated sensor that includes applying or depositing an amount of a coating material without entraining bubbles in the coating material on a chemically bondable fluid contacting surface of a sensor. The coating material includes a solvent, a soluble poly-oligomer having a fluorine containing groups and an aliphatic ether ring in the chain of the poly-oligomer, and the poly-oligomer has reactive groups. The reactive groups on the poly-oligomer are used for bonding the poly-oligomer to the chemically bondable fluid contacting surface of the sensor. The method has a step of removing solvent from the coating material applied to the chemically bondable fluid contacting surface of the sensor to form a non-porous film of the coating material. The formed non-porous film includes greater than 10% of the poly-oligomer in the coating material originally applied to the fluid contacting surface of the sensor. The method has a step of curing the non-porous film of the coating material on the chemically bondable fluid contacting surface of the sensor. The curing chemically bonds at least a portion of the reactive groups of the poly-oligomer to the chemically bondable surface of the sensor surface to form an adherent non-porous protective coating on the chemically bondable fluid contacting surface of the sensor. The method may be used on chemically bondable fluid contacting surface of the sensor that may be but is not limited to a ceramic, a mineral, a poly-oligomer, a metal or a combination of these. Curing occurs at a temperature less than the boiling point of the coating material solvent and less than the Tg of the poly-oligomer film and may include ramping the temperature up to a value greater than the boiling point of the solvent and greater than the Tg of the poly-oligomer material to remove any remaining solvent and to enhance the adhesion of the coating to the ceramic substrate. Preferably the curing step occurs at a temperature below which damage to the electronic structures on other surfaces of the sensor can occur, even more preferably the curing temperature is less than 120° C. Chemical and photochemical treatments of the non-porous film may be used to cure it to the sensor surface. The chemically bondable fluid contacting surface of the sensor used in the method may be treated with an adhesion promoter or an organosilane to form the chemically bondable fluid contacting surface of the sensor. The method may be used to coat one or more sensors, each sensor having a chemically bondable fluid contacting surface. The coating material can be applied to each sensor by a dispenser having one or more nozzles. The chemically bondable fluid contacting surface of the sensor used in the method may include a ceramic material or a ceramic material with a coating on it. The method preferably results in an effective thickness of an adherent non-porous coating on a surface of the sensor which protect it and structures formed on it from corrosion, particle generation, delamination, swelling, or changes in sensor response and sensitivity caused by the fluid and even more preferably has a thickness of greater than 50 microns and even more preferably greater than or equal to 100 microns. The method of coating may be used for a sensor which includes a diaphragm. The solvent removal step of the method may be performed in an antistatic environment. The curing step of the method may include but is not limited to chemical, photochemical, thermal curing or a combination of these. The sensor, coated by the method, may include structure on one or more of its surfaces chosen from the group consisting of resistive, capacitive, transistors, electrical contacts, optical contacts, or a combination of these.

Advantages of the present invention include the ability to form thick non-porous protective coatings on a variety of substrates in a single deposition step. The invention permits a variety of sensors, cuvettes, flexible bellows members, gas cells, optical window, material handling devices and housings, to be coated and used in hostile and corrosive environments. Preferably the adherent non-porous coating protects the underlying structures from corrosion, particle generation, delamination, or changes in sensor response and sensitivity caused by the fluid. In some cases less expensive but more sensitive versions of sensors can be coated with the protective and adherent film and used in corrosive and hostile environment reducing costs and improving performance. The coating process is simple and results in fluid applied to a substrate that can be treated to form non-porous films of the poly-oligomer suitable for curing. The process minimizes waste and chemical consumption and reduces overall cost while maintaining or improving overall performance achieved through the use of low cost sensors. The ability to coat multiple sensors or other fluid contacting structures and to simplify the manufacturing process because devices can be coated having leads, electronics, and bond pads already formed on the structures by the use of a low temperature curing process condition is advantageous.

The defect free and adherent thick coatings made by the present invention provide greater chemical and mechanical resistance than thinner coatings applied to similar structures because diffusion and chemical permeability decrease as coating thickness increases. The ability to make such coatings in a single step makes the use of such coatings advantageous because of they are easy to manufacture and cost effective because multiple sensors may be coated and material waste minimized.

DESCRIPTION OF THE DRAWINGS

In part, other aspects, features, benefits and advantages of the embodiments of the present invention will be apparent with regard to the following description, appended claims and accompanying drawings where:

DETAILED DESCRIPTION

Figure 1:
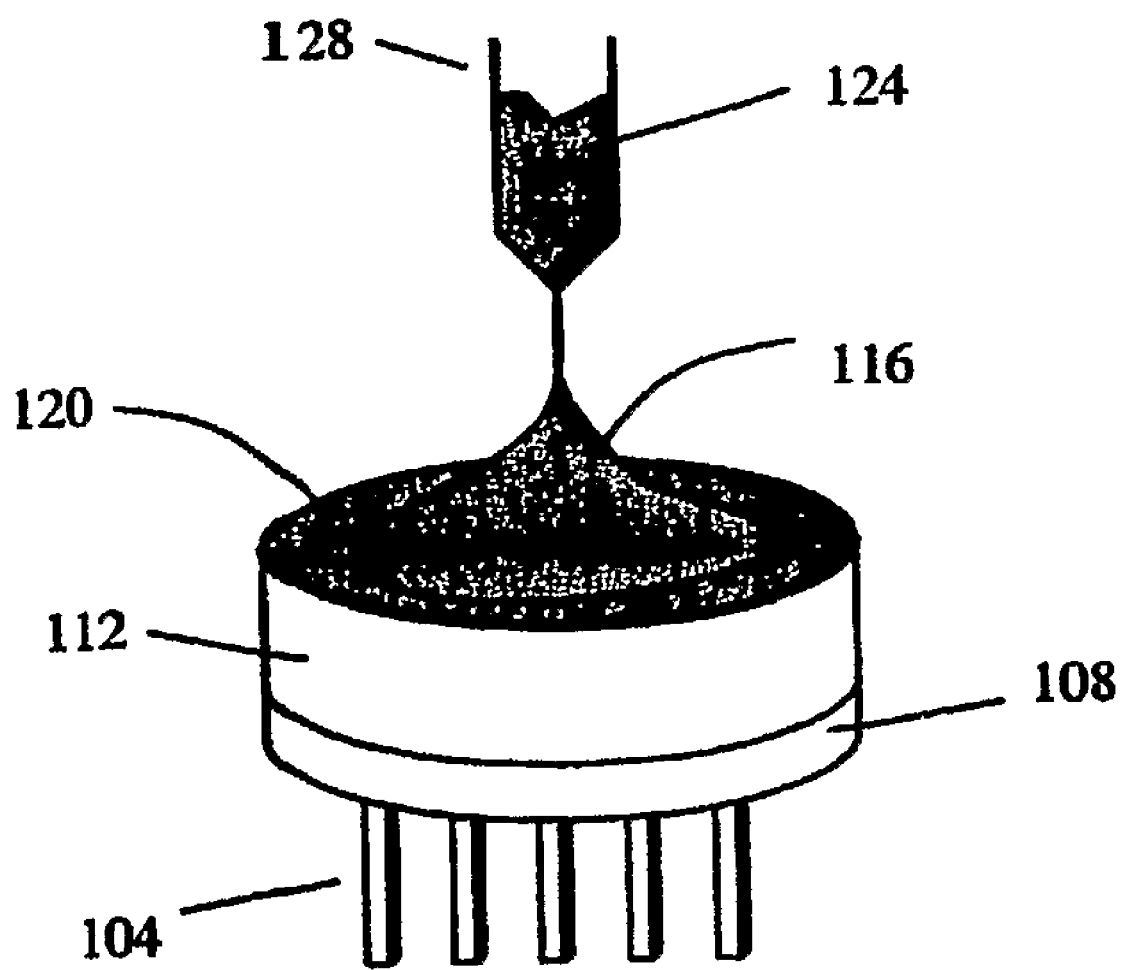
FIG. 1 illustrates a sensor or substrate with a coating material being dispensed without bubbles onto the substrate surface from a nozzle, electrical or optical feed-through connected to the substrate are also shown.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "coating poly-oligomer molecule" is a reference to one or more coating poly-oligomer molecules and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

"Optional" or "optionally" means that the subsequently described event or circumstance may or may not occur, and that the description includes instances where the event occurs and instances where it does not.

Embodiments of the present invention may include adherent coatings of chemically inert high purity poly-oligomers on sensor and other substrates. The coatings are applied and cured on the sensor or other substrates at relatively low temperatures which permits the coating process to be performed with temperature sensitive substrates having low melting points, magnetic properties, or sensitive electronics for conversion of the substrate properties into electrical signal. Structures of the present invention include those having an effective thickness of a protective non-porous coating that is adherent and chemically bonded to a surface of the structure in contact with a fluid. Structures may separately include but not limited to a sensor, a conduit, heat exchange conduits, a vessel such as a cuvette or gas sampling cell, mixers, bellows, impellers, diaphragms, fluid material handling, or wafer handling equipment, or transparent windows that are to be contacted with a fluid during chemical processing, transport, handling, or characterization, or combinations of these. The fluid can be one whose properties are to be measured or characterized. The protective and adherent coating is chemically inert, has low permeability to fluids, ions and gases. An effective thickness adherent non-porous coating on a surface of the sensor protect it and structures formed on or within the substrates such as magnets, electrodes and electrical structures from corrosion, particle generation, delamination, swelling, or other physical and chemical changes that may adversely affect the performance or operation of the underlying coated substrate.

FIG. 1 illustrates a sensor or substrate surface 120 with a coating fluid 124 being dispensed without drops or bubbles 116 onto the substrate surface 120 from a nozzle 128. Optional electrical or optical feedthroughs 104 connected to the substrate are shown. The substrate surface may be mounted to one or more base or backing plates 108 and 112 or may be machined or formed from a single substrate.

Figure 2:
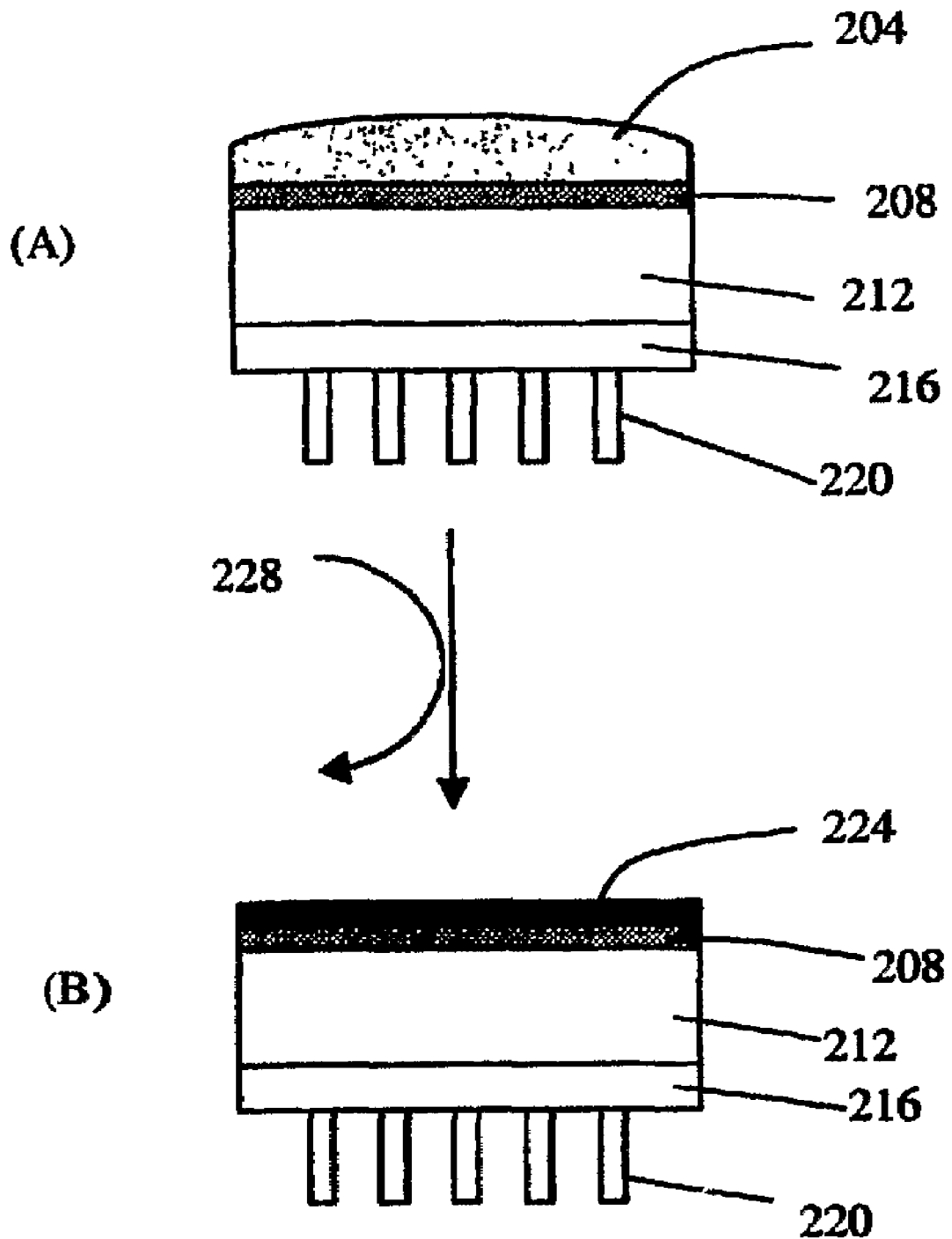
FIG. 2 (A) illustrates a bubble free volume of coating material deposited onto the surface of a substrate, (B) shows that coating conformally covering a sensor substrate of the present invention after evaporation of solvent to form a non-porous film suitable for curing.

FIG. 2(A) illustrates, in cross section, a bubble free volume of poly-oligomeric coating material 204 deposited onto a sensor or substrate surface 208 after dispense. The sensor or substrate 208 may be mounted, formed, or machined into one or more base structures 212 and 216. Optional electrical or optical feedthroughs 220 are shown. FIG. 2(B) shows a non-porous film coating 224 covering the sensor or substrate 208 of the present after evaporation of solvent in step 228. The non-porous film 224 is suitable for curing and in some embodiments is a conformal coating on the substrate 208. The sensor or substrate 208 may be mounted or machined into one or more base structures 212 and 216. Optional electrical or optical feedthroughs 220 are shown.

Figure 3:
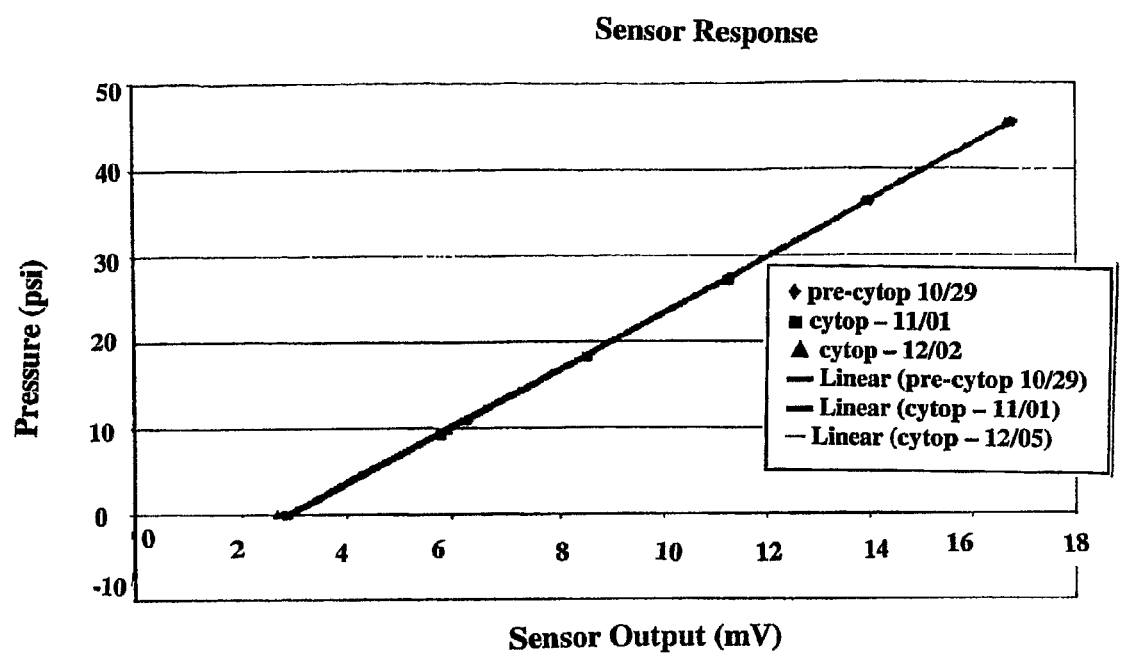
FIG. 3 shows calibration data for sensors with and without the adherent non-porous coating of the present invention at various times.

FIG. 3 shows calibration data for a sensor with and without the adherent non-porous coating of the present invention at various times. The slopes of the calibration curve are nearly identical and indicate that the uncoated sensor had nearly the same sensitivity as the sensor after coating and that the sensitivity of the coated sensor does not change over the period of time.

Figure 4:
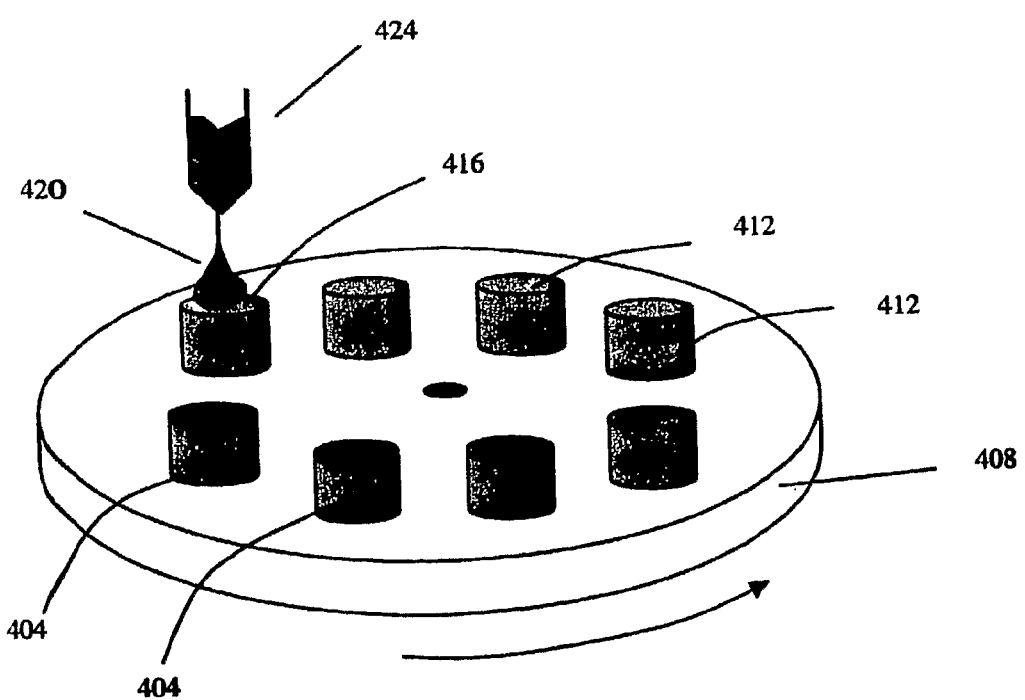
FIG. 4 illustrates a process and apparatus for coating multiple substrates on a rotatable stage with a coating material dispensed from a nozzle onto the substrate surfaces to form adherent non-porous coating on the substrates.

FIG. 4 illustrates an embodiment of a coating process and apparatus for coating multiple substrates on a moving stage 408. The movable stage 408 has one or more uncoated substrates 412 mounted on the stage that may be coated with a coating material 420 from a dispense nozzle 424 delivered, without drop or bubbles, onto the substrate surfaces 416. Coated substrates 404 with poly-oligomer are shown on the movable stage 408. The coated substrates 404 do not have bubbles and may be treated to evaporate the solvent from the coating.

Figure 5:
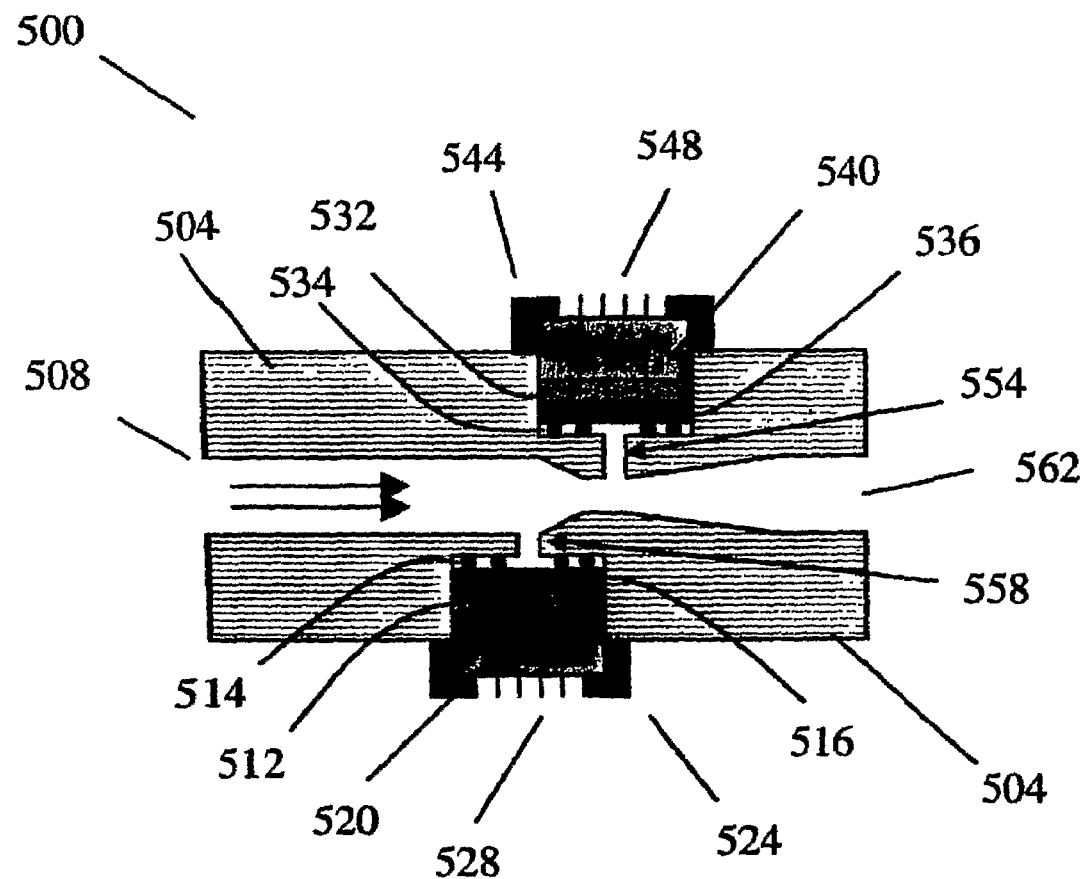
FIG. 5 illustrates sensors having non-porous adherent coating configured in a housing, shown in cross section, for measuring the property of a fluid; the housing can be mounted in a fluid flow circuit and has inlet and outlet ports for connection to the fluid flow path.

FIG. 5 illustrates a device 500 shown in cross section having sensors with a non-porous adherent coating on a surface of the sensor; the sensors are configured in a housing 504. The coated sensors may be used for measuring the property of a fluid. The housing 504 can be mounted in a fluid flow circuit and has inlet port 508 and outlet port 562 for connection to a fluid flow path. The housing 504 may have one or more ports, 554 and 558 that allow contact between a fluid (not shown) and the sensors. Surfaces of the housing may be coated with an adherent non-porous coating of the present disclosure. The layer of non-porous inert coating bonded to the sensors, 516 and 536 may be fluidly sealed against the housing or body 504 using one or more chemically compatible and compliant gaskets 514 and 534. Port 554 permits contact of fluid with sensor having an adherent non-porous coating 536 on a substrate 532 mounted to base 540. Base 540 may be held to housing or body 504 by retainer 544. Port 558 permits contact of fluid with sensor having an adherent non-porous coating 516 on a substrate 512 mounted to base 520. Base 520 may be held to housing 504 by retainer 524. Feedthroughs for electrical connection or optical fibers for each sensor, 528 and 548, are also illustrated.

FIG. 6A illustrates a sensor substrate 608 having a non-porous adherent coating of a poly-oligomer containing fluorine 604 on the outer surface 610 of a sensor substrate 608. In some embodiments the structures 602 for measuring the physical response of the sensor surface 608 that will contact a fluid are not covered by the protective coating 604. In some embodiments where the structures 602 for measuring the physical response of the sensor surface 608 may be covered by a protective coating 604. The structures 602 for measuring the physical response of the sensor may be bonded to the substrate 608 and connected by optical or electrical elements 614 through the base 612. A portion of the inner surface 606 of the sensor substrate 608 may be bonded to a base 612. The sensor base 612 is shown with a vent 616. FIG. 6B illustrates a substrate 642 with a diaphragm 626 formed in the substrate 642. The surface 630 of the diaphragm 626 has a non-porous adherent coating 624 of a poly-oligomer containing fluorine. The substrate 642 may be bonded to a second substrate 632, the second substrate 632 is shown with a vent 636. In one embodiment the edges of the substrates 608 and base 612 may be coated with the coating material 604 to provide corrosion resistance and protection to the bonded region between the base 608 and substrate 612.

Figure 7:
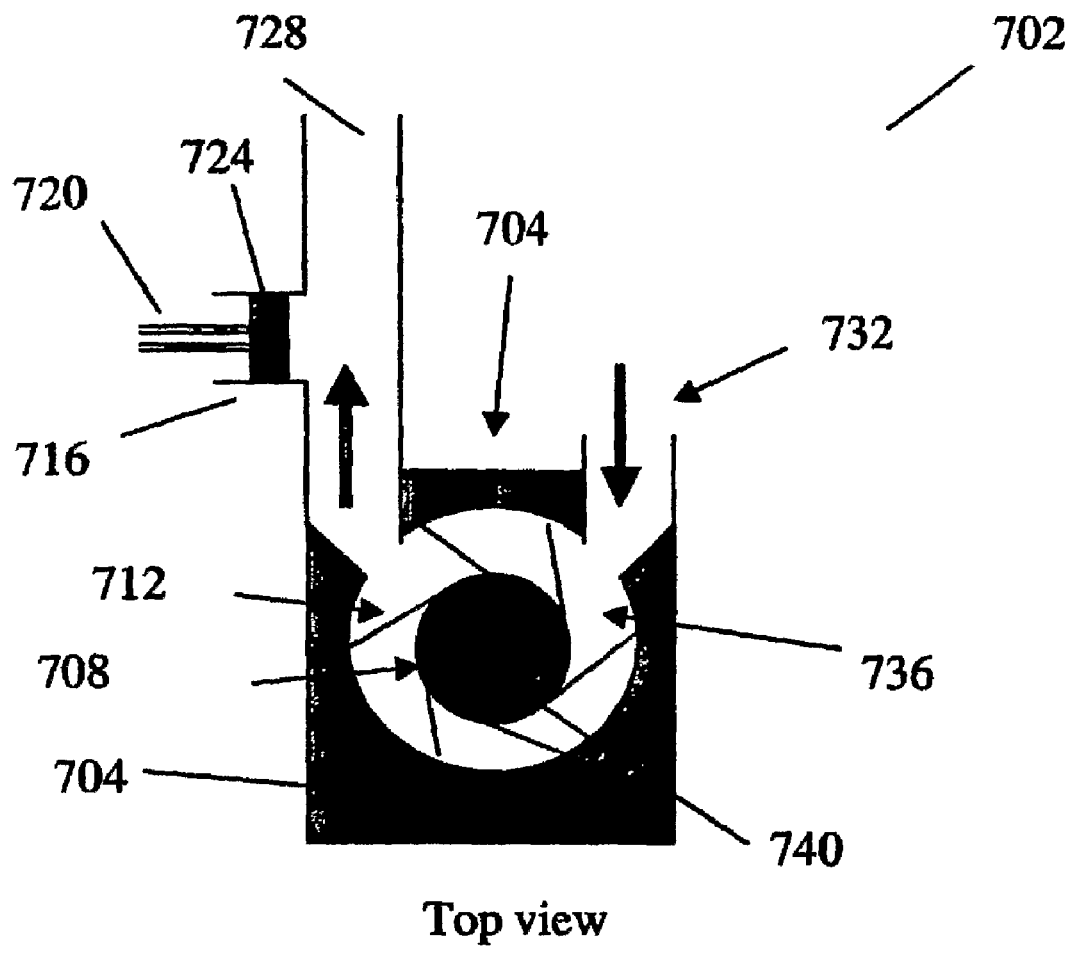
FIG. 7 illustrates a fluid handling device having one or more sensors, portions of the surfaces of the sensor and or fluid handling device may be coated with a non-porous adherent inert coating.

FIG. 7 illustrates a top view of a device 702 that handles or conditions a fluid. One or more portions of the fluid contacting surfaces of the fluid handling device may be coated with a non-porous adherent coating of a poly-oligomer containing fluorine. The fluid handling device includes a base 704, a housing interior 736 that contacts the fluid. As illustrated, the device 702 may be used for transporting a fluid from the inlet 732 to the outlet 728 using an impeller 708 with vanes 712 and impeller magnets 740. Alternatively the fluid may be transported or conditioned using tubes, gears, diaphragms, or other structures. The vanes 712 or other structures may be coated with the non-porous adherent coating. The device 702 has an outlet 728 and an inlet 732 that contact the fluid and may be used for connection to conduits in a fluid flow circuit. Optionally the device may include one or more sensors 724 coated with a non-porous adherent coating of a poly-oligomer containing fluorine. The sensor 724 with leads 720 may be mounted to a port 716 and may be used to measure a property of a fluid handled or conditioned by the device 702.

The housing or base 704 has at least one fluid chamber 736 that is in fluid communication with a fluid inlet 732 and a fluid outlet 728. The housing or base 704 has one or more structures 712 or 724 that can with a fluid in the chamber. One or more surfaces of the housing 704 or the structures that interact with the fluid 712 and 724 can have an effective thickness of a non-porous fluorine containing poly-oligomer coating adherent on at least a portion of the surfaces.

The coating may be applied to various devices that include a housing having at least one fluid chamber, the chamber in fluid communication with a fluid inlet to the housing and the chamber in fluid communication with a fluid outlet from the housing. The chamber can include one or more structures capable of interacting with fluid in the chamber such as a flow sensor, a conduit, a housing, elements of a fluid pump, elements of a flow meter or flow controller, a flexible member such as a bellows, or an impeller. One or more surfaces of structures in the device, such as but not limited to the housing, the chambers, the inlet and outlet, bellow, impellers, pressure sensor, conduits, and combinations of these can have an effective thickness of a non-porous adherent protective coating on at least a portion of a surface, the coating protecting the surface from a fluid, the coating including a soluble poly-oligomer containing fluorine, and being chemically bonded to the surface. The device may have structures interacting with the fluid in the chamber that can be a diaphragm, a bellows, an impeller, a sensor or combinations of these. The device housing, chamber, and structures can interact to form a pump, a valve, a fluid flow meter, a heat exchangers, or a fluid flow controller. The housing, chamber, and structures can interact o form a valve. The housing, chamber and structures can interact to form a fluid flow meter. The housing, chamber, and structures of the device can interact to form a fluid flow controller.

Bellows can used to create a seal around a moving part such as vertical driver and may be used in a variety devices like pumps, valves, and robotic arms. In pumps for example, when pressurized air is directed by a valve through a first conduit to the interior of a cylinder in contact with a piston that is surrounded by a bellows, the bellows is raised and the extension of the bellows can be used to dispense a liquid through an outlet via a check valve and to transport liquid through a connection to a first liquid chamber. The pressurized air can then be directed by the valve into a second conduit, releasing pressure on the cylinder interior and used to lower or contract the bellows to discharge liquid in the liquid chamber and to draw fluid from a source into a second liquid chamber separates from the first by the connection. This cycle of directing pressurized air into the first and second conduits can be repeated to pump a liquid. By fabricating a valve seat in the housing and a stem on the end of the bellows, a similar cycle could be used to open and close a valve. Bellows may have a high surface area and their motion can trap contaminants, require long purge times, create stress in the bellows. Further, corrosion of the bellows can result in particle generation. Bellows may be coated with a an adherent non-porous coating. The adherent coating includes a soluble poly-oligomer containing fluorine where a portion of the poly-oligomer is chemically bonded to the bellows surface to form an adherent protective coating. The adherent coating may be formed by curing a non-porous film of the coating material formed or placed on the surface of the bellows.

Other objects, such as encased magnetic stirrers, magnetic pump impellers, magnetically levitated impellers, or heat exchange surfaces, when used in an ultrapure but corrosive environment, require a superior chemically resistant, non-permeable, and low diffusion coating. Coating methods for devices such as these and others which require a 360 degree coating may be drip coated, immersion coated, or coated while magnetically suspended in place. In the case of drip or immersion coating, a second coating may be necessary where supports were used in the first coating to ensure a defect free final coating.

To obtain wet chemical coatings with low surface roughness, it may be desirable to carry out the coating in a cleanroom, and to filter the coating liquid. Proper cleaning of the substrates is also important to remove grease, surface contaminants, and other particulates that may affect coating adhesion.

Dip coating techniques can be used to coat various substrates with the fluorine containing coating solution. In this process the substrate, or portion of the substrate, to be coated is immersed in a liquid and then withdrawn with a well-defined withdrawal speed under controlled temperature and atmospheric conditions. The conditions are chosen to reduce or eliminate the entrapment of gases or bubbles in the coating. The coating thickness is mainly defined by the withdrawal speed, by the coating concentration (monomers, solids, gels, oligomers) and the viscosity of the liquid. In one embodiment, the coating thickness is mainly defined by the withdrawal speed, by the coating concentration of a soluble poly-oligomer containing fluorine, and the viscosity of the liquid including a soluble poly-oligomer containing fluorine. Withdrawal speeds of substrates being coated in a dip-coat process can range from as low as about 0.1 mm/min up to about 3 cm/second although other ranges are possible. The withdrawal speed of the object to be coated (conduit, sensor, bellows, housing, impeller, stirrer, mixer, portions of these, and combinations of these) may be chosen such that the sheer rates of the coating composition keeps the system in the laminar flow regime. Under these conditions it may be possible to estimate the desired coating thickness using Landau-Levich equation and routine experimentation. Variations in the coating thickness may also be achieved by changing the viscosity of the coating solution and or the solution density. The atmosphere surrounding the item being coated controls the evaporation rate of the solvent and influences the formation of the final film. The addition, removal, or modification of solvent vapor pressure near the substrate or object to be coated can also be used to control the coating thickness.

An angle-dependent dip coating process can be used to coat the objects or substrates. In this process the coating thickness can be changed by modification of the angle between the substrate and the liquid surface. In this process, the substrate or object can be rotated at an angle in a vessel containing the coating material. Slow rotation may be used to eliminate entrapment of bubbles in the coating applied to the object. Layer thickness and uniformity can be calculated and related to the dipping angle, withdrawal rate, and rotation rate for the substrate. These coating variables can be changed to obtain an adherent non-porous coating of the fluorine containing material on the object that may be further cured to form a layer that is non-porous and chemically bonded to the substrate. The adherent non-porous layer protects the underlying object surfaces from fluids that would adversely affect the underlying substrate surface (corrosion, delamination, particle generation, swelling, weakening, generation of contamination).

The coating material may be deposited, applied, or dispensed onto the substrate by low temperature coating processes that preferably minimize or eliminates waste of the coating material. Examples of such coating method may include but are not limited to knife over roll coating, die cast coating, immersion coating, curtain coating, and air knife coating. Where coating of the substrate utilizes a nozzle, the nozzle can be positioned over the substrate and in a proximity to the substrate so the coating material from the nozzle contacts the surface of the substrate in a continuous stream. One method for avoiding bubble generation in coating material deposited on a substrate may be to minimize the velocity of the coating solution as it is transferred from pipette or nozzle to a substrates such as diaphragm by careful pipetting or nozzle dispense technique. Dispense pumps such as the Intelligen® from the Mykrolis Corporation, syringe pumps such as the Harvard Model 22, or automated micropipetters can be used to dispense fluid onto substrates. The stream of fluid without the formation of drops also provides for thick coating films and minimize the entrainment of bubbles in the films; drop may lead to voids and corrosion paths in the coating. Multiple dies may be used for coating multiple substrates or the substrates may be moved under the die on a moving or rotating table as illustrated in FIG. 4 or a conveyer. The coating can be deposited onto the substrate at a rate so that a meniscus of the liquid forms on the substrate; this is illustrated by coating volume 204 on substrate 208 shown in FIG. 2A.

The coating is preferably applied to the substrate by a method or process which minimizes and preferably eliminates the amount of coating material which is lost or wasted during the coating process. For example, in the application of coating material onto a planar electrode, the coating material may be dispensed from a nozzle onto a stationary or slowly rotating electrode in a single continuous stream until the substrate is covered with the coating material. Alternatively a dip coating process or a flow coating process can be used. The liquid is allowed to evaporate to leave a non-porous conformal film of the coating on the substrate. By comparison, a spin coating process, while it may be used to distribute dispensed coating material across a substrate, is less desirable because up to about 99% of the coating fluid dispensed onto the coating surface is lost during spin up.

Substrates may be coated in a flow coating process where the liquid coating composition is essentially poured over the substrate to be coated. The coating thickness depends on the angle of inclination of the substrate with the liquid coating composition dispense stream, the coating liquid viscosity and the solvent evaporation rate. Flow coating processes may be used to recapture coating material that does not adhere to the substrate and reduce coating waste. The atmosphere of the chamber with the object and bath may be controlled and solvent or gases added to control evaporation. Using the flow-coating process, non-planar large substrates can be coated rather easily. As a variation of this process, the spinning of the substrate after coating may be helpful in order to obtain more homogenous coatings.

High purity poly-oligomers containing fluorine or coatings made from them of are preferably those which do not contribute amounts materials that may be considered contaminants in the fluid to be contacted with the coated substrate. Preferably the coating materials or the cured coatings contribute less than 1000 ppb v/v of materials considered to be contaminants to the fluid contacted by the coated substrate. Examples of such contaminants may include ions, water or organic solvents, or particulates. Soluble coating materials or formed coatings may be analyzed as neat samples or following extraction using mass spectroscopic techniques, elemental analysis, HPLC, or other techniques. Where it is difficult to obtain high purity soluble coating materials, ion exchange or extraction of deposited coating may be performed to make coatings with acceptable levels of purity. In some embodiments the purity of the coating material including but not limited to hydrocarbons, metal ions, and anions is selected to prevent unwanted contamination of fluids measured by a coated sensor of the present invention. It may also be possible to clean deposited films for example by chemical extraction or vacuum baking and degassing to achieve a higher purity in finished films.

The protective and adherent coating is chemically inert, has low permeability to fluids, ions and gases. An effective thickness adherent non-porous coating on a surface of the sensor protect it and structures formed on or within the substrates such as magnets, electrodes and electrical structures from corrosion, particle generation, delamination, swelling, or other physical and chemical changes that may adversely affect the performance or operation of the underlying coated substrate. In one embodiment an effective thickness of the coating protects the substrate from corrosion above 25° C. In another embodiment an effective thickness of the coating protects the substrate from corrosion at about 50° C. or above. A coating of a non-porous fluorine containing poly-oligomer applied to the surface of a substrate may be tested by exposure to corrosive fluids for its ability to protect the underlying substrate from damage. Substrates coated with varying thickness of coating can be exposed to the corrosive fluid and the fluid analyzed for ions, chemicals, or particles from the substrate material. The test with the fluid and coated substrate may be performed at room temperature or at higher temperatures. The corrosive fluid may be analyzed using particle counters, ICP mass spectroscopy, or HPLC. The substrate may be inspected using microscopy and gravimetric analysis.

The coating material is a chemically inert poly-oligomeric material having low surface energy, below about 40 dynes/cm, low chemical permeability to dissolved ions, liquids, and gases, low mass change, and is essentially incompressible. The poly-oligomer chain has pendant groups that contain fluorine and can be dissolved in a solvent. The protective films preferably are those which can be characterized as having a gas permeability less than Teflon AF® for a test gas such as oxygen or nitrogen. Non-porous adherent films of the present invention may be characterized for permeation through a sample of the membrane film in contact with a temperature controlled volume of fluid and the permeation or diffusion through the film measured as a function of temperature, fluid properties, or film thickness. Detection can be performed by connecting the outside of the membrane to a detection system like and FTIR spectrometer or an APIMS.

Bonding pads may be on one or more surfaces of the substrate and used to provide for input and output of electrical and or optical signals from the substrate to processors, amplifiers, through wires or optical fibers. Holes filled with a glass or epoxy 618 in the backing plate can connect wires or optical fibers 614 to the sensor element 602. An example of such a sensor is a strain gauge where the resistive elements are applied to the surface of the sensor, for example 602, that is not in contact with the fluid to be measured. The element 602 may be fabricated on the diaphragm surface 606 in FIG. 6A or on surface 626 (element not shown) in FIG. 6B. In the case of an optical pressure sensor, for example, bonding pads and or electronics are not present on the surface of the substrate. In this case the substrate surface itself or the surface with a reflective coating may be used for measurement.

In some embodiments the substrate is a pressure sensor that may be constructed as a piezoresistive or capacitance sensor having a sensing diaphragm. The sensing diaphragm can be made of a etched silicon, a ceramic, a metal, or sapphire. The sensor may have a backing plate, sensing diaphragm, silica glass bond between the backing plate and diaphragm, and electrical leads connected to sensing elements.

A pressure sensor may include a backing plate, a non-porous diaphragm, a sensing element adjacent an inner surface of the diaphragm, and a glass layer of a high strength material that is bonded by glassing to the backing plate and the non-porous diaphragm. The backing plate provides rigidity to the structure. The rigidity of the backing plate resists stresses transmitted from the housing to the sensing elements on the sensor diaphragm. Although the backing plate is not in direct contact with the process medium it is mechanically stable and amenable to high temperature processes. The thermal expansion rate of the backing plate can closely approximate that of the sensing diaphragm. While it is possible to compensate for thermal effects, a large mismatch will produce stresses during manufacture that may cause the bond between the two pieces to yield over time. Those skilled in the art will appreciate that the non-porous diaphragm may include a Wheatstone bridge or a conductive layer formed on it as part of a piezoresistive or capacitive type sensor respectively.

To form a piezoresistive sensor, a silicon layer can be formed on an inner surface of the diaphragm, wherein a strain gage such as a Wheatstone bridge is formed. The backing plate includes apertures extending through it, the apertures being adapted and may contain optical and or electrical leads coupled to the sensing element. A change in pressure near the diaphragm is detectable by the sensing element. An increase and decrease of pressure against the diaphragm causes deflection of the diaphragm which in turn changes the resistances of the strain gauge. The changes in resistance is correlated with the pressure adjacent the diaphragm. The pressure sensor may be constructed such that the sensing element may detect an absolute pressure or gauge pressure.

The pressure sensor may includes bond pads formed on the piezoresistive sensing element deposited on the diaphragm. In an alternate embodiment the diaphragm and sensing element is modified to create a capacitance rather than a piezoresistive sensor. The thin sensing diaphragm, which flexes when pressure is applied, has a capacitive plate formed on the inner surface of the sensing diaphragm and another capacitive plate is formed on the inner surface of the backing plate. One electrical lead is connected to the capacitive plate formed on the inner surface of the sensing diaphragm and another lead is electrically coupled to the inner surface of the backing plate. As the spacing between the diaphragm and the plate vary with pressure the capacitance of the plates changes. This variation in capacitance can be detected by an electrically connected circuit element of known suitable construction.

In yet another alternative embodiment the diaphragm and sensing element are modified to accept an optical fiber. The optical fiber measures the change in shape of the diaphragm as it changes with pressure. This variation in diaphragm shape is detected by light energy from the optical fiber reflected from the fluid isolated side of the diaphragm and related to fluid pressure.

Methods, means, and structures for exciting sensors and detecting a response are described. Examples of such are disclosed in U.S. Pat. Nos. 6,681,787, 'System and method of operation of a digital mass flow controller', Tinsley, et al; 6,640,822, 'System and method of operation of a digital mass flow controller' Tinsley, et al; 6,617,079, 'Process and system for determining acceptability of a fluid dispense', Pillion, et al; 6,596,148, 'Regeneration of plating baths and system therefore', Belognia, et al; 6,575,027, 'Mass flow sensor interface circuit', Larsen, et al; 6,527,862, 'Flow controller', McLoughlin, et al; 6,449,571, 'System and method for sensor response linearization', Tarig, et al; 6,445,980, 'System and method for a variable gain proportional-integral (PI) controller', Vyers; the contents of each of these patents are incorporated herein by reference in their entirety.

Examples of soluble poly-oligomers containing fluorine which may be used as coating material include those disclosed in U.S. Pat. No. 6,201,085 the contents of which are incorporated herein by reference in their entirety. These coating materials include those which are a perfluoro-poly-oligomer obtained by the cyclo-poly-oligomerization of perfluoro (alkenyl vinyl ether). These poly-oligomers containing fluorine are soluble in organic solvents due to their amorphous structure, and may be coated onto a substrate. In one embodiment the soluble fluorine containing poly-oligomers are onto a substrate without entrained bubbles. In another embodiment the soluble fluorine containing poly-oligomers are onto a substrate without entrained bubbles and where loss of the soluble poly-oligomer during the coating process is less than 90% or less than 10% from the amount deposited on the substrate. The substrate may be any material with which the material can form an adherent film. For example, the substrate may be treated with an adhesion promoter such as an aminosilane coupling agent and then coated with the perfluoro-poly-oligomer. Alternatively the end groups of the perfluoro-poly-oligomer are modified to provide chemical groups that provide adhesion to the substrate as disclosed in U.S. Pat. No. 5,498,657 the contents of which are incorporate herein by reference in their entirety. For example, the endgroups of the poly-oligomer chain may be modified with an organo-silane which can be used to bond the modified perfluoro-poly-oligomer to the substrate. The use of an adhesion promoter or chemically modified poly-oligomers reactive with the substrate or sensor provides adhesion of the poly-oligomer to the substrate. By reacting with substrate surface, the groups may help to reduce corrosion of the substrate surface. Other useful soluble poly-oligomers containing fluorine pendent groups for coatings may include those disclosed by French et. al, Journal of Fluorine Chemistry, vol 122 (2003). The endgroups of these poly-oligomers can be chemically modified to promote bonding with the substrate surface or may be combined with an adhesion promoter to form adherent films with the substrate.

The use of an adhesion promoter avoids the disadvantages attendant upon forming separate barrier/passivation layers and separate adhesion layers. In accordance with the present invention, any of various commercially available adhesion promoters can be employed, such as but not limited to silane-based organic adhesion promoters. Suitable commercially available silane-based adhesion promoters include 3-APS (3-aminopropyltriethoxysilane) or MOPS (3-methacryloxypropyltrimethoxysilane). Other commercially available silane-adhesion promoters containing vinyl, chloropropyl, epoxy, diamine, mercapto and/or cationic styryl organofunctional groups can be employed. Where chemically acceptable, non-silicon adhesion promoters containing for example aluminum, gallium, or other elements may be used.

The coating material dissolves in a solvent. The coating material may include fluorine containing poly-oligomers with alicyclic structures in its main chain and preferably fluorine containing aliphatic ether ring structures in its main chain. The chain of the poly-oligomer in the coating material may have reactive groups for bonding to the substrate. The coating material poly-oligomer may have molecules such as but not limited to amino functionalized organosilanes dissolved in the coating material that may bond to the substrate and to reactive groups on the poly-oligomer chains for bonding the poly-oligomer to the substrate. The coating material poly-oligomer may have reactive groups for bonding to the substrate and for bonding with other poly-oligomer chains.

The molecular weight of the poly-oligomer in the coating material may be used to tailor the coating for surface coverage, adhesion, strength, and chemical permeability. The concentration of the poly-oligomer used in the coating solution will affect its dispense, viscosity, and the thickness of a formed film for a given amount of coating material deposited on a substrate. The concentration of poly-oligomer in the solution depends upon the molecular weight of the poly-oligomer, but may be less than about 50% and is preferably less than about 25% by weight. The density of the adherent non-porous coating film on the substrate may be controlled by the concentration of the poly-oligomer in the coating solution as well as by its molecular weight. Increasing the poly-oligomer concentration, use of mixtures of fluorine containing poly-oligomers, or increasing the molecular weight may also be used to change film density The coating material includes poly-oligomeric molecules and may be used to refer to both polymeric molecules and one or more linked oligomeric molecules. The present invention may be practiced with oligomeric molecules, or a mixture of oligomers and poly-oligomers. Oligomers which may be used include those fluorine containing molecules with reactive groups similar to those present in the poly-oligomer or poly-oligomeric molecule disclosed herein and especially those reactive groups which may be used to form higher molecular weight poly-oligomeric species upon thermal, chemical, or photochemical curing of an oligomeric coating material.

Materials for coating the substrates, and preferably sensor substrates, of the present invention may include those which cure and adhere by chemical bonding to the substrate, form defect free (for example no cracks, voids, or bubbles) films of sufficient thickness to provide the substrate with chemical protection and not attenuate or significantly attenuate the sensitivity of the sensor or physical properties of the substrate in its application. In some embodiments, the interaction of the coating with fluids is minimal, for example no swelling or adsorption that would modify the sensor response; the coating provides the sensor substrate with chemical protection against corrosion or degradation. The materials may be applied at temperatures and processing conditions which are compatible with sensors and substrates having electronic circuitry formed on a portion of the substrate or other temperature sensitive elements like magnets. Curing the non-porous film can occur at a temperature less than the boiling point of the coating material solvent and less than the Tg of poly-oligomer film. This can be optionally followed by ramping the temperature of the substrate with the coating up to a value greater than the boiling point of the solvent and greater than the Tg of the poly-oligomer material to remove any remaining solvent and to enhance the adhesion of the coating to the substrate, preferably a ceramic substrate. It is desirable that the coating form a uniform film that adheres to the sensor substrate at temperatures below about 200° C. and more preferably below about 120° C.

The temperature for drying or removing the fluorine-containing solvent from the fluorine containing poly-oligomer can be selected depending upon the heat resistance of the substrate, and may range from 15° C. to about 150° C.; and preferably is below 35° C. In one embodiment, the temperature during evaporation can be in the range of from about 15° C. to about 50° C. and provides for a crack free film of the uncured poly-oligomer to form on the sensor substrate. The evaporation parameters to form the non-porous film may be determined by thermogravimetric analysis of the coating material at different temperatures and gas flow conditions. The evaporation time will depend upon the amount of material, the vapor pressure of the solvent(s), surface area, temperature of the substrate and surrounding environment, and flow rate of gases. These may be modified as would be known to those skilled in the art, however the formed film is free of defects (crack, voids, bubbles). To prevent an irregular film thickness the solvent may be removed in an antistatic environment. Evaporation of solvent from the coating material composition forms a non-porous film of the poly-oligomer from the coating material on the substrate. This is shown schematically in the step labeled 228 between FIG. 2A and FIG. 2B. Preferably the film of the coating material on the substrate is non-porous so that fluids or particles cannot pass through the film except by permeation or diffusion. The coating material film on the substrate, and preferably a non-porous film, may be cured to form a non-porous adherent film of the coating material on the surface of the substrate. Long curing times may be used to achieve reaction of the adhesion promoter at lower temperatures. Lower curing temperature permits substrates with deposited electronics to be coated and processed directly which provides for low cost production methods and permits less expensive electronics to be used.

During the dispense and subsequent evaporation of solvent from the coating material applied to the substrate, the composition of the atmosphere surrounding the substrate and coating may be controlled. This may include but is not limited to control of the temperature, flow rate of gas across the coated substrate, composition of the gas to include reactive gases as well as solvent vapor, the use of an antistatic environment or a combination of any of these.

Once the poly-oligomer has formed a self supporting film on the substrate, for example 224 in FIG. 2B, the self supporting film may be cured to promote adhesion of the poly-oligomer to the substrate. For example it is desirable that the coating form a uniform film that adheres to the sensor substrate at temperatures below about 200° C. and more preferably below about 120° C. The curing temperature may be slowly ramped up to the curing temperature to avoid rapid solvent outgassing and bubble formation. Ramping the temperature up to a value greater the boiling point of the solvent and greater the Tg of the fluorine containing poly-oligomer removes remaining solvent in the film and may be used to cause the terminal groups of the fluorine containing poly-oligomer to further react, either with the ceramic substrate, promoting adhesion, or internally, crosslinking and increasing chemical resistance. This process can be carried out in an oven capable of increasing the process temperature at a rate of about 5° C./hour, or about 10° C./hour or more provided that bubbles or cracks are not form in the film as temperatures above the solvent boiling point and poly-oligomer glass transition temperature are exceeded. After heating the non-porous film on the substrate to a temperature above the solvent boiling point and poly-oligomer glass transition temperature, the substrate is allowed to soak at the final temperature for about 2 hours or sufficient time to chemically bond the film to the substrate. The time required to sufficiently bond the film to the surface of the substrate may vary depending upon the substrate, final temperature, and reactivity of the adhesion promoting groups but can determined by measuring the non-porous film adhesion with a standard tape test after various temperature and times for heating. An inert gas purge may be used during the evaporation and heat treatment processes.

When water vapor or any other condensable vapor is absorbed by a poly-oligomer film, the physical properties of the film, such as mass, thickness, surface resistance, volume resistance, and dielectric constant, can change. These changes, which can be detected by various techniques, may be used to characterize the desirability of various coating materials for their intended use. For instance, changes in the quantity of water absorbed in humidity-sensitive films can be measured as changes in 1) the resonant frequency of a surface acoustic wave or a mechanically resonant structure coated with the film, 2) the surface or volume resistance between two electrodes connected to the film, or 3) the capacitance between sandwich-electrode or interdigitated-electrode capacitors employing the film as dielectric.

A very wide range of substrates may be provided with a non-porous adherent coating in accordance with the instant invention. Almost any organic or inorganic solid material may be suitable as a substrate, including metal, glass, ceramic semiconductors, rubber, natural and synthetic resins. In one embodiment substrates containing temperature sensitive components and materials are substrates. These temperature sensitive components may include magnetic materials, electronic and optical structures, solders, composite materials with differing coefficients of thermal expansion, flexible, molded, or shaped items. Especially useful are those substrates which have reactive groups, such as but not limited to hydroxyl and carboxylic acid groups that can be used to chemically react with and bond to a portion of the fluorine containing poly-oligomeric molecules in the coating material or an added adhesion promoter. The process of the invention is also suited for encapsulation of electrode and electronic components. The adherent non-porous films coating a portion of the substrates in contact with a fluid bonds to the surface and reduces or is non-permeable to fluids and ions in fluids which degrade or corrode the underlying substrate. The degradation may affect the physical or chemical properties of the underlying substrate for its intended purpose. The non-porous fluorine containing poly-oligomer coating on the substrate may be used to prevent the release of degradation products, such as but not limited to particles, molecules, and ions, from the underlying substrate into the process fluid.

Sensors which may be coated by the materials and methods of the present invention are preferably those on which a layer of poly-oligomer may be applied to form a thick bubble free film of the poly-oligomer on the sensor such as but not limited to die cast, aerosol spray coat, dip coating, or a combination of these. The substrates may be coated in a single step, however more that one coating step may be used to achieve a desired film thickness or to coat substrates where it is not practical to coat the entire object in a single step. Where the substrates are planar, they may include channels or raised structures on their surface. The sensor substrates may have a surface which have reactive groups or may be chemically treated such as by plasma, pre-coating, or chemical methods to form groups on the sensor surface that can further react with reactive groups on poly-oligomer molecules in the coating material to bond a portion or all of the poly-oligomer to the substrate. The poly-oligomer molecules in addition to bonding with the substrate surface, may also react with each other to form a cross linked structure. The reaction of the reactive groups of the poly-oligomer with each other or with the surface may be initiated by thermal, photochemical, or chemical treatments. For example, the thermal treatment of the substrate and poly-oligomer film can result in hydrolysis reactions between the substrate and reactive groups on the poly-oligomer.

Figure 6:
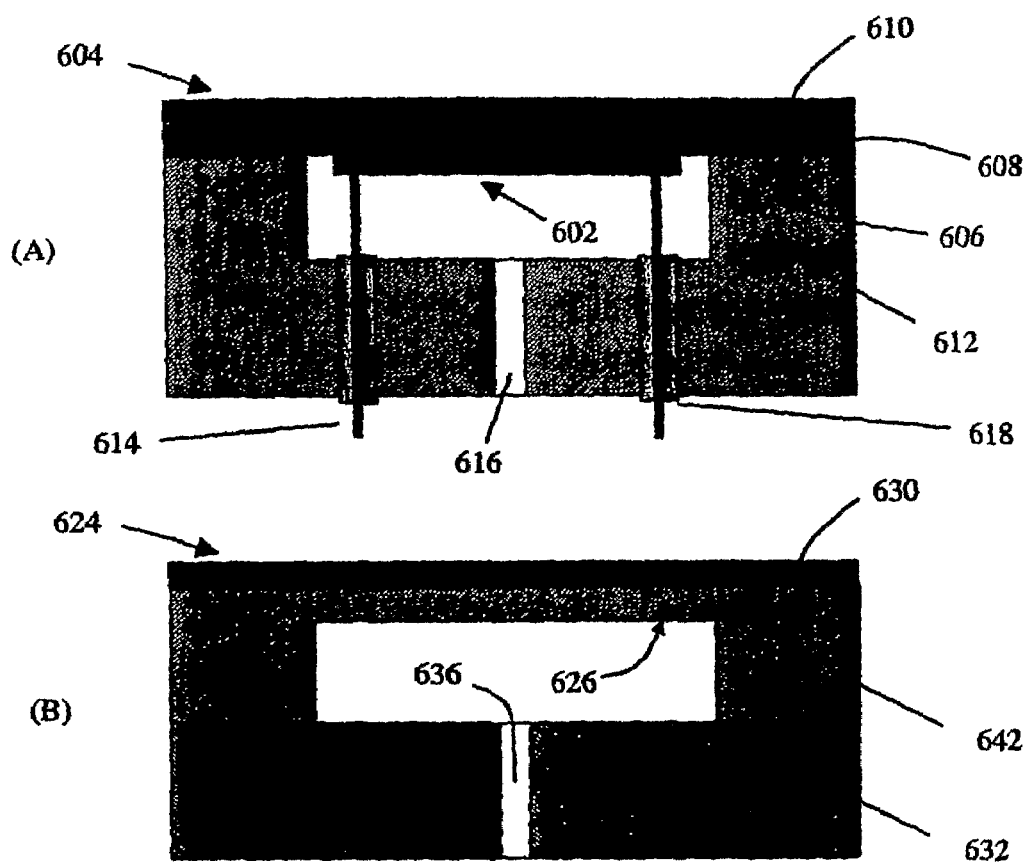
FIG. 6A-B illustrates a substrate having a non-porous adherent coating on the surface opposite the sensor base.

The coating can also help to preserve the physical integrity of a fluid system by maintaining a fluid tight seal when there is a mechanical failure of the coated substrate. For example, if a gauge type of ceramic pressure sensor is exposed to a pressure condition in excess of its pressure rating, there is a possibility that the brittle sensing diaphragm may fail and allow the process fluid to escape from the fluid system through the sensor's atmospheric vent, potentially causing damage to nearby equipment, or endangering the health of people in the area. If, as illustrated in FIG. 6, the sensor diaphragm 608 is coated with a defect free, adherent material 604 that is flexible and extensible, fluid system integrity may be maintained in case of diaphragm failure and loss of fluid through the vent 616. The coating may also prevents contamination of the fluid system in the case of failure of the coated component.

Where the substrate includes one or more material interfaces between different materials, a poly-oligomer coating material may be applied to the substrate and one or more interfaces to provide chemical and mechanical advantages to the substrate and interfaces. Preferably each of the surfaces are capable of or have been treated to react with an adhesion promoter or the poly-oligomer molecules in the poly-oligomer coating material to effect adhesion of the coating material to the substrate. Thermal, photochemical, or chemical reaction or a combination of these may be used to react the surfaces with coating to effect adhesion.

For optically transparent poly-oligomer films, a chemically sensitive material may be incorporated into a portion of the poly-oligomer molecules, or the chemically sensitive material may be incorporate into the surface of the poly-oligomer film. A change in color or absorption for example may be detected by light absorbed or reflected from the coating to indicate the presence or absence of desirable or deleterious molecules in the fluid. Optical windows may be coated by the fluorine containing poly-oligomer coating material composition to provide chemical and physical protection to the window.

The substrates coated by the poly-oligomer may include but are not limited to pressure sensors including strain gauges, capacitive based pressure sensors, and fiber optic or laser diode based pressure sensors that measure changers in a property, such as intensity, of light or electromagnetic energy reflected from the diaphragm surface. The substrate may serve as a support for the poly-oligomer film and any chemically sensitive material incorporated thereon. For optical applications, the substrate and film can be optically transparent in the wavelength region used for detection. The sensor may be used to measure the temperature of a fluid and the poly-oligomeric coating used to prevent or substantially reduce ions and fluid from reaching the temperature probe.

The sensors of the present invention may be mounted in a housing to contact the sensors with a fluid whose property is to be measured. The housing may be made of a chemically suitable material, preferably a material which is chemically inert to the fluid. Some housing materials may include a coating of the poly-oligomeric material applied to a portion or all of the housing surfaces. The poly-oligomer coated sensor or optical window in a housing or vessel may be mounted to or in the housing or vessel using methods and materials known to those skilled in the art including but not limited to compression seals using o-rings, gaskets, and fusion bonding. The housing may be placed in contact with the fluid by submersion or the housing may have inlet and outlet fluid ports for mounting the sensor in fluid communication with fluid in a conduit. The windows may be those in a gas cell used for the analysis of chemical composition of fluids, the adherent non-porous coating protecting the windows and gas cell from corrosion and particle generation.

The coated sensors may be combined to form flowmeters and other measuring devices such as but not limited to temperature compensated pressure sensors, flow meters, and flow rate compensated chemical sensors.

Various aspects of the present invention will be illustrated with reference to the following non-limiting examples.

EXAMPLE 1

This example illustrates coating a sensor substrate with a fluorine containing poly-oligomer to form an adherent non-porous coating on the sensor. The coating does not affect the sensitivity of the sensor.

CYTOP® available from Asahi Glass was coated onto Metallux ceramic pressure sensors. CYTOP® is a fluorine containing polymer containing an aliphatic ether ring structure in its main chain. The CYTOP® coating on the Metallux ceramic pressure sensor formed an integral coating and include applying the poly-oligomer solution onto the sensor without entraining air bubbles and slowly ramping up to the curing temperature to avoid rapid solvent outgassing and bubble formation.

Calibration data from a single Metallux pressure sensor; uncoated, with a 2.5 mil (0.0063 cm) CYTOP coating and with a 5 mil (0.013 cm) CYTOP coating showed that there was no significant difference between the sensitivity for any of the conditions (uncoated, 2.5 mil, or 5 mil) as illustrated in FIG. 3.

Metallux data show an offset shift less than 0.2% full scale after 2,000, 000 F.S. pressure cycles and an offset shift of less than 0.05% full scale after 110 hours at 82° C.

EXAMPLE 2

This example shows that the fluorine containing poly-oligomer coating can provide high purity coating and that the thickness of the coating may be used to reduce leaching of contaminants from a coated substrate. The coating protects the underlying substrate from corrosion by the fluid.

Evaluation of chemical compatibility of Metallux pressure sensors coated with Cytop® resin. Extractables data was acquired from tests using HCl, tetramethylammonium hydroxide (TMAH), and DI water.

The extractables levels from the tests run with DI water were all very low. The results from both the TMAH and HCl showed higher levels of aluminum and the TMAH showed high levels of lead. In both chemicals, the aluminum and lead levels were higher in the sensors coated with a 2.5 mil (0.0063 cm) thick layer of Cytop®, compared to the sensors coated with a 5 mil (0.013 cm) thick layer of Cytop®. The aluminum levels from both chemicals were highest in the aluminum buttons coated with a 5 mil thick layer of Cytop®.

These tests were run using ten Teflon housings, each of which was designed to hold two Metallux pressure sensors. With the sensors installed, each unit can hold approximately 1.5 ml of fluid. When installed, the face of each of the two sensors is in contact with the fluid.

Four different materials were tested: Teflon dummy sensors with the same dimensions as the pressure sensors were used for a baseline, aluminum buttons with the same dimensions as the pressure sensors coated with a 5 mil (0.013 cm) layer of Cytop®, Metallux pressure sensors coated with a 5 mil (0.013 cm) layer of Cytop®, and Metallux pressure sensors with a 2.5 mil (0.0063 cm) layer of Cytop®. Three different chemicals were used: deionized water, 10% hydrochloric acid, and 2.5% tetramethyl ammonium hydroxide (TMAH). A description of the material and chemical tested in each unit is shown in Table 1.

Prior to the start of the experiment, the Teflon enclosures, the Kalrez o-rings used to seal the sensors in the units, and the Teflon dummy sensors were pre-extracted over night in 10% HCl. Once the materials and chemicals were installed in each unit, the ten units were placed in a 50° C. oven for one month. Periodically during the month, the units containing the aluminum buttons were tested for resistance. A multimeter was used to test the resistance across the two aluminum buttons in each of these units. No increase in resistance was observed during any of the measurements indicating that measurable amounts of ions were not generated by diffusion or permeation of ions through the films. At the end of the month, all of the chemical samples were submitted for extractables testing. Sensors were extracted for 30 days in 10% HCl. Extraction volume was 1.5 mL. Samples were analyzed for metals using ICPMS. Sensors were extracted for 30 days in TMAH. Extraction volume was 1.51 mL. TMAH extractions were prepared for analysis by hotplate evaporation and reconstitution in $HNO_3$. Samples were analyzed for metals using ICPMS. Sensors were extracted for 30 days in water. Extraction volume was 1.5 mL. Samples were analyzed for metals using ICPMS.

The extractables results are reported in units of ug/unit, where a unit is one housing containing two sensors. The extractables levels from tests run with DI water were all below 1 ug/unit. The highest extractables were seen from the Cytop®-coated aluminum button, in which the sodium level was 0.63 ug/unit, the potassium level was 0.59 ug/unit, and the calcium level was 0.24 ug/unit.

The extractables levels from tests run with HCl were all below 1 ug/unit, except for aluminum. The aluminum levels were highest from the Cytop-coated aluminum button (5.41 ug/unit). The aluminum levels from the 2.5 mil (0.0063 cm) Cytop®-coated sensor (3.51 ug/unit) were much higher than those from the 5 mil (0.013 cm) Cytop®-coated sensor (0.15 ug/unit). The aluminum levels from the 5 mil (0.013 cm) Cytop®-coated sensor were lower than those from the Teflon button (0.42 ug/unit).

The extractables levels from tests run with TMAH were all below 1 ug/unit, except for aluminum and lead. The aluminum levels were highest from the Cytop®-coated aluminum button (6.59 ug/unit). The aluminum levels from the 2.5 mil (0.0063 cm) Cytop®-coated sensor (2.18 ug/unit) were five times higher than those from the 5 mil (0.013 cm) Cytop®-coated sensor (0.42 ug/unit). The aluminum levels from the 5 mil (0.013 cm) Cytop®-coated sensor were close to those from the Teflon button (0.31 ug/unit). The lead levels were very small in the Teflon button and Cytop®-coated aluminum button (0.01 ug/unit). The lead levels from the 2.5 mil (0.0063 cm) Cytop®-coated sensor (2.19 ug/unit) were three times higher than those from the 5 mil (0.013 cm) Cytop®-coated sensor (0.69 ug/unit).

TABLE 1

| Test Unit | Material | Coating Thickness (mil) | Coating Defects | Chemical |
|---|---|---|---|---|
| 1 | Aluminum #1 | 5 | Small dot on outer edge | DI Water |
|   | Aluminum #2 | 5 | None |  |
| 2 | Sensor #C02482/1-8 | 5 | Small dot on outer edge | DI Water |
|   | Sensor #C02482/1-12 | 5 | Small dot on outer edge |  |
| 3 | Teflon | N/A | N/A | HCl |
|   | Teflon | N/A | N/A |  |

TABLE 1-continued

| Test Unit | Material | Coating Thickness (mil) | Coating Defects | Chemical |
|---|---|---|---|---|
| 4 | Aluminum #6 | 5 | None | HCl |
|  | Aluminum #4 | 5 | None |  |
| 5 | Sensor #C02482/1-13 | 5 | Small dot on outer edge | HCl |
|  | Sensor #C02482/1-9 | 5 | Small fibrous imperfection near edge |  |
| 6 | Sensor #C02482/1-16 | 2.5 | None | HCl |
|  | Sensor #C02482/1-15 | 2.5 | None |  |
| 7 | Teflon | N/A | N/A | TMAH |
|  | Teflon | N/A | N/A |  |
| 8 | Aluminum #3 | 5 | None | TMAH |
|  | Aluminum #5 | 5 | None |  |
| 9 | Sensor #C02300/1-10 | 5 | Small dot on outer edge | TMAH |
|  | Sensor #C02300/1-11 | 5 | None |  |
| 10 | Sensor #C02482/1-14 | 2.5 | None | TMAH |
|  | Sensor #C02482/1-17 | 2.5 | None |  |

EXAMPLE 3

This example illustrates a method used to coat a substrate with a bubble free volume of fluorine containing poly-oligomer.

Using volumes of Cytop® coating material greater than about 200 μl, the coating material solution can be spread across a sensor surface that is an octagon shape with an edge to edge length across the sensor of about 0.654 inches (1.66 cm) and area 0.35 square inches (2.26 cm$^2$).

To avoid generation of small bubbles in the Cytop® coating applied to the sensor surface, these bubbles expand upon heating and create void or porous films, the pipette was not blown out after dispense. The pipette tip was held just above sensor/coating surface to let solution drops spread on the surface without producing bubbles and better still without producing individual drops that could fall onto the volume of coating on the substrate. The solvent was allow to evaporate for at least 30 min. before heating in an oven. A longer evaporation time could be used for second and subsequent coats.

EXAMPLE 4

This example describes coating substrates which are pressure sensors with a non-porous coating of a fluorine containing polyoligomer with an aliphatic ether ring structure in its main chain.

METALLUX 501 ceramic sensors were coated with Cytop® perfluoropoly-oligomer, available from Asahi Glass Company. CYTOP™ is a perfluoro-polymer obtained by the cyclopolymerization of perfluoro(alkenyl vinyl ether and contains fluorine bonded to the carbon chain.

The purpose of coating the wetted surfaces of a ceramic pressure sensor with CYTOP® perfluoropoly-oligomer is to enhance the chemical resistance of these surfaces thereby minimizing the risk of contaminating the process fluid coming into contact with the sensor. These sensors are less costly to use and produce than sapphire diaphragms for pressure sensors.

The coating process in this example includes the steps of: cleaning and dehydrating the surface(s) to be coated, applying a bubble-free coating of CYTOP® P(er)F(luoro)P(olymer) solution to the sensor surface, allowing the bulk of the solvent to evaporate at room temperature, soft baking the sensor at a temperature less than the boiling point of the coating material solvent and less than the Tg of CYTOP PFP to remove most of the remaining solvent, and ramping the temperature up to a value greater than the boiling point of the solvent and greater than the Tg of the CYTOP material to remove any remaining solvent and to enhance the adhesion of the coating to the ceramic substrate. For coatings thicker than can be applied to the surface in one coat, the steps of applying, evaporating, and curing can be repeated as needed to achieve the desired thickness prior to the final bake or curing cycle.

Cleaning and dehydrating the surface to be coated can be performed to ensure good adhesion between the sensor and the CYTOP® coating, the surfaces to be coated (sensor diaphragm) should be scrubbed with an acetone wet wipe to remove any organic material and then flushed with a squirt (~1 ml.) of acetone to remove any remaining particulate material. The sensor should then be baked in a 110° C. oven for 60 minutes to drive off any moisture. At the end of the bake cycle, the hot sensor can be placed in a dessicator to cool, and remain in the dessicator until coated.

Applying a bubble-free coating of CYTOP® PFP (PerFluoroPoly-oligomer) solution to the diaphragm. The coating material is 'CTL-107M', a 7% (by weight) solution of Asahi's 'M' CYTOP perfluoropoly-oligomer (low molecular weight grade) in CT-SOLV100, a perfluoroalkane (primarily perfluoro-octane).

The coating process utilizes sensors mounted, diaphragm up, in a fixture having an 18 mm diameter recess to locate the device. A 15.25 mm. diameter thru hole in the center of the recess provides clearance for the electrical connectors/cables. The recess is level to provide a uniform coating thickness. If the sensor has an electrical cable, the center of mass of the cable falls within the vertical extension of the sensor's O.D. to prevent tilting of the sensor in the fixture.

Once the sensor is properly fixtured, a volume of CYTOP® solution sufficient to cover the entire diaphragm surface, but not enough to overcome the surface tension forces at the edges of the diaphragm and allow the solution to spill over the edges, is applied to the diaphragm using a precision microliter pipetter. It was experimentally determined that at least 200 μl. of solution was needed to completely cover the diaphragm surface. (The use of more dilute CYTOP 107M solutions resulted in coating thickness variations on the active surface [minimal thermal mass] area of the diaphragm, apparently due to evaporative cooling effects).

Exclude or immediately remove any bubbles from the solution on the diaphragm as they will form defects (pinholes or thin spots) in the coating. One method of avoiding bubble generation is minimizing the velocity of the solution as it is transferred from pipette to diaphragm by careful pipetting technique. Also, the 1 ml. pipetter tips used in the coating process have a very small opening at the tip which can result in high solution dispense velocities and the entrainment of air bubbles in the coating. By cutting back the tapered pipetter tip by about 5 mm., the diameter of the tip opening is increased enough to minimize the generation of bubbles due to high dispense velocities. Visible bubbles in the liquid coating may be moved to the edge of the diaphragm with the pipetter tip or sucked into the pipetter; however these actions my result in the formation of small, visually undetectable bubbles which eventually become defects in the coating.

Allow the bulk of the solvent to evaporate at R.T. After the bubble-free coating of CYTOP® PFP solution has been applied to the sensor diaphragm, the bulk of the CT SOLV-100 is allowed to evaporate at R.T. for approximately 30 minutes before moving the sensor. This will result in a sensor with a physically stable coating precursor which can be safely transferred to the 'softbake' or curing oven.

'Soft' baking the sensor at a temperature less than the boiling point of the solvent and less than the Tg of CYTOP® to remove most of the solvent. The boiling point of the CT-SOLV100 solvent is about 100° C. and the Tg of the CYTOP poly-oligomer is 108° C. The purpose of this process step is to remove most of the solvent in the coating without initiating further reaction of the poly-oligomer's end groups in preparation for additional coatings or the final bake step. This step is preferentially carried out with the sensor in the same (or a similar) fixture as used in the coating process to keep the sensor essentially level while ramping up from a temperature of 40° C. to a temperature of 60° C. over a period of 60 minutes.

The three previous coating, evaporation and soft bake steps may be repeated as needed to achieve the desired final coating thickness Ramping the temperature up to a value greater the boiling point of the solvent and greater the Tg of CYTOP removes remaining solvent in the film and enhance the adhesion of the coating film to the substrate. The purpose of this step is to remove any remaining solvent from the diaphragm's coating and to cause the terminal groups of the CYTOP 'M' poly-oligomer to further react, either with the ceramic substrate, promoting adhesion, or internally, crosslinking and increasing chemical resistance. This process is carried out in an oven capable of increasing the process temperature at a rate of about 5° C./hour from 60° C. to 125° C., followed by a 2 hour 'soak' at 125° C.

EXAMPLE 5

This prophetic example illustrates an example of a material handling device used for transporting fluid that has one or more structure coated with an adherent non-porous coating. The device includes a housing that can be used to mount one or more optional sensors and include fluid inlet and fluid outlet connections.

The material handling device may be coated and used in hostile and corrosive environments. The adherent non-porous coating applied to the device protects the underlying structures from corrosion, particle generation, delamination, or changes operation caused by the fluid. The ability to coat multiple fluid contacting structures and to simplify the manufacturing process because devices can be coated having leads, electronics, bond pads, or temperature sensitive magnetic elements already in or already formed on the structures is possible by the use of a low temperature curing process condition. Lower cost materials may be used, for example, to make an impeller that can then be coated with the fluorine containing coating. Fully encapsulated impellers can be prepared at low temperatures.

The material handling device illustrated in FIG. 7 is an impeller pump. Structures of the impeller pump that can be coated with the non-porous adherent coating of a fluorine containing oligomer may include but are not limited to one or more optional sensors 724 mounted to the housing 704, the interior of an inlet 732 or an outlet conduit 728, the inner surfaces of the housing vessel 736, and fluid handling impellers 712. The impellers may be fixed or flexible.

The impeller structure, or portions of it, for example vanes 712, or vanes and supporting structure with magnets 740, may be coated. An adhesion promoter can be used to pre-treat the impeller surface. The impeller can be coated by angle dependent dip coating with slow rotation the portion of the impeller below the rotation shaft of the impeller (shaft not shown in FIG. 7) in a solution of CYTOP® PFP (PerFluoroPoly-oligomer). This coating material can be CTL-107M, a 7% (by weight) solution of Asahi's 'M' CYTOP perfluoropoly-oligomer (low molecular weight grade) in CT-SOLV100, a perfluoroalkane (primarily perfluoro-octane). The rotation rate for coating can be chosen to prevent entrapment of gas during submersion of the object and to facilitate coalescence and rising of bubbles on the impeller in the coating solution. Stands having through holes for the rotation shaft may be used to cure the first coating. The rotation shaft may be dip coated in the same solution in a second step.

The impeller pump may be use to handle fluids such as slurries and corrosive liquids. The coating methods of this example may be applied to other material handling devices such as diaphragm pump surfaces, bellows pump surfaces, mixing blades, metal heat exchangers, and other surfaces of fluid handling devices where a low cost protective coating is needed to protect the underlying substrate from particle generation, corrosion, or degradation.

Although the present invention has been described in considerable detail with reference to certain preferred embodiments thereof, other versions are possible. Therefore the spirit and scope of the appended claims should not be limited to the description and the preferred versions contain within this specification.

What is claimed is:

1. An article comprising:
a sensor substrate including a non-porous adherent protective coating on a portion of a surface of the sensor substrate, the non-porous adherent protective coating protects the sensor substrate from corrosion by a fluid above 25° C. in contact with the non-porous adherent protective coating, the non-porous adherent protective coating includes a fluorine containing poly-oligomer that is chemically bonded to the surface of the sensor substrate, the non-porous adherent coating has a thickness of greater than 50 microns.

2. The article of claim 1 where the non-porous adherent coating protects the sensor substrate from corrosion by said fluid above 50° C.

3. The article of claim 1 including an adhesion promoter.

4. The article of claim 1 where the non-porous adherent coating material includes fluorine containing poly-oligomers with alicyclic structures.

5. The article of claim 1 where the sensor substrate further includes structures on one or more surfaces of the sensor, said structures chosen from the group consisting of resistive, capacitive, transistors, electrical contacts, optical contacts, or a combination of these.

6. The article of claim 1 wherein the slope of a calibration curve for the sensor including said non-porous adherent protective coating and a slope of a calibration curve for a sensor without said non-porous adherent protective coating are nearly identical and have an offset of less than 0.2% full scale.

7. The article of claim 1 wherein the non-porous adherent coating has a thickness of more than 100 microns.

8. A coated sensor comprising:
a sensor with a non-porous adherent coating on a surface of the sensor, said coating contacts a fluid, said sensor with the non-porous adherent coating includes structures for measuring the physical response of the sensor in contact with the fluid, the non-porous adherent coating includes a fluorine containing poly-oligomer that is chemically bonded to the sensor surface, the non-porous adherent coating has a thickness of greater than 50 microns and said non-porous coating protects the sensor from corrosion above 25° C. in the fluid.

9. The coated sensor of claim 8 wherein the non-porous adherent coating is free of voids.

10. The coated sensor of claim 8 where the sensor is a pressure sensor and is a ceramic material.

11. The coated sensor of claim 8 where the sensor is temperature sensor, a flow sensor, a chemical purity sensor, a pressure sensor, or a combination of these.

12. The coated sensor of claim 8 where the fluid is 10% HCl (pp. 32,) and the coating protects the sensor from corrosion at 50° C. in said fluid.

13. A method comprising:
   removing solvent from an amount of a bubble free coating material applied on a chemically bondable fluid contacting surface of a sensor substrate to form a non-porous coating on the fluid contacting surface of said sensor substrate, the amount of said bubble free coating material includes a solvent and soluble fluorine containing poly-oligomers, the fluorine containing poly-oligomers have reactive groups that chemically bond the poly-oligomer to the surface of the substrate, said non-porous coating on the fluid contacting surface of said sensor substrate has a thickness of greater than 50 microns.

14. The method of claim 13 where the non-porous coating on the fluid contacting surface of said sensor substrate includes greater than 10% of the poly-oligomer in the amount of bubble free coating material applied to the surface of the substrate.

15. The method of claim 13 further including the act of curing the non-porous coating on the fluid contacting surface of said sensor substrate, the curing chemically bonds the reactive groups of the poly-oligomer to the chemically bondable fluid contacting surface of the sensor substrate to form an adherent non-porous coating on the chemically bondable fluid contacting surface of the sensor substrate.

16. The method of claim 13 wherein the chemically bondable fluid contacting surface of the substrate is a pressure sensor.

17. The method of claim 15 where the curing occurs at a temperature less than the boiling point of the solvent and less than the Tg of poly-oligomer.

18. The method of claim 15 further including the act of increasing the temperature of the non-porous coating on the fluid contacting surface of said sensor substrate up to a value greater than the boiling point of the solvent and greater than the Tg of the poly-oligomer material.

19. The method of claim 13 wherein said chemically bondable fluid contacting surface of the sensor substrate includes an organosilane that is capable of reacting with the fluorine containing poly-oligomers.

20. The method of claim 13 where the solvent removal occurs in an antistatic environment.

21. The method of claim 13 where the amount of bubble free coating material applied on the chemically bondable fluid contacting surface of a sensor substrate includes an adhesion promoter.

* * * * *